United States Patent [19]

Linz et al.

[11] Patent Number: 5,817,677
[45] Date of Patent: Oct. 6, 1998

[54] 5-MEMBERED HETEROCYCLES, MEDICAMENTS CONTAINING THESE COMPOUNDS, THEIR USE AND PROCESSES FOR THEIR PREPARATION

[75] Inventors: Günter Linz; Frank Himmelsbach, both of Mittelbiberach; Helmut Pieper; Volkhard Austel, both of Biberach; Brian Guth, Warthausen; Johannes Weisenberger, Biberach, all of Germany

[73] Assignee: Dr. Karl Thomae GmbH, Biberach, Germany

[21] Appl. No.: 733,898

[22] Filed: Oct. 18, 1996

[30] Foreign Application Priority Data

Oct. 20, 1995 [DE] Germany .................. 195 39 091.1
Dec. 27, 1995 [DE] Germany .................. 195 48 798.2

[51] Int. Cl.⁶ .................. A61K 31/455; A61K 31/41; C07D 417/04; C07D 285/12
[52] U.S. Cl. .................. 514/326; 514/252; 514/318; 514/360; 544/365; 546/187; 546/209; 546/268.7; 548/136
[58] Field of Search .................. 544/365; 546/187, 546/209, 268.7; 548/136; 514/252, 318, 326, 360

[56] References Cited

U.S. PATENT DOCUMENTS 5,668,159 9/1997 Jin et al. .................. 546/209 X

FOREIGN PATENT DOCUMENTS 0 525 629 2/1993 European Pat. Off. .
0 608 858 8/1994 European Pat. Off. .
WO 95 14683 6/1995 WIPO .
WO 96 20173 7/1996 WIPO .

Primary Examiner—Fiona T. Powers
Attorney, Agent, or Firm—Robert P. Raymond; Alan R. Stempel; Mary-Ellen Devlin

[57] ABSTRACT

5-Membered heterocyclic compounds, of which the following compounds are exemplary:

(a) 4-[[trans-4-(2-carboxyethyl)cyclohexyl]aminocarbonyl]-1-(4-piperidyl)imidazole,
(b) 5-[[trans-4-(2-carboxyethyl)cyclohexyl]aminocarbonyl]-4-methyl-2-(4-piperidyl)-1,3-thiazole,
(c) 5-[[4-(carboxymethoxy)phenyl]aminocarbonyl]-4-methyl-2-(4-piperidyl)-1,3-thiazole,
(d) 5-[[trans-4-(2-carboxyethyl)cyclohexyl]aminocarbonyl]-2-(4-piperidyl)-1,3,4-thiadiazole,
(e) 5-[[4-(carboxymethoxy)phenyl]aminocarbonyl]-2-(4-piperidyl)-1,3,4-thiadiazole,
(f) 5-[[trans-4-(carboxymethoxy)cyclohexyl]aminocarbonyl]-2-(4-piperidyl)-1,3-thiazole,
(g) 5-[[4-(carboxymethoxy)phenyl]aminocarbonyl]-2-(4-piperidyl)-1,3-thiazole,
(h) 5-[[trans-4-(2-carboxyethyl)cyclohexyl]aminocarbonyl]-2-(4-piperidyl)-1,3-thiazole, and
(i) 4-[[trans-4-carboxycyclohexyl]aminocarbonyl]-1-[2-(4-piperidyl)ethyl]imidazole.

These are useful for the treatment or prevention of illnesses in which relatively small or relatively large cell aggregates occur or cell-matrix interactions play a part.

8 Claims, No Drawings

5-MEMBERED HETEROCYCLES, MEDICAMENTS CONTAINING THESE COMPOUNDS, THEIR USE AND PROCESSES FOR THEIR PREPARATION

WO 95/14683, EP-A-0,525,629 and EP-A-0,608,858 already describe 5-membered heterocycles which have useful pharmacological properties, preferably aggregation-inhibiting effects.

It has now been found that the novel 5-membered heterocycles of the general formula

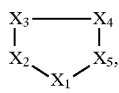 (I)

also have useful pharmacological properties.

The present invention thus relates to the above 5-membered heterocycles of the general formula I, which differ from the 5-membered heterocycles known from the literature by the radicals D and E, to tautomers thereof, to stereoisomers thereof including mixtures thereof and salts thereof, in particular physiologically tolerable salts thereof with inorganic or organic acids or bases, which have useful pharmacological properties, preferably aggregation-inhibiting effects, medicaments containing these compounds, their use and processes for their preparation.

In the above general formula I one of the radicals $X_1$ to $X_5$ is a group of the formula

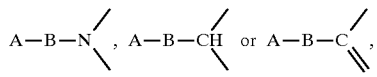

in which

A is a cycloalkyl group having 5 to 7 carbon atoms, which is optionally substituted by 1 to 4 alkyl groups, in which an unsubstituted methylene group is replaced by the $R_a$—N< group, which can additionally be substituted by a cyano, aminocarbonyl, carboxyl, alkoxycarbonyl or phenylalkoxy-carbonyl group or alternatively, if the substitution does not take place in the α-position relative to a nitrogen atom, by a hydroxyl, alkoxy or phenylalkoxy group, and in which $R_a$ is a hydrogen atom, an alkyl group, a phenylalkyl group, an alkoxycarbonyl group having a total of 2 to 6 carbon atoms, a phenylalkoxycarbonyl group, an alkenyloxycarbonyl group having a total of 4 to 6 carbon atoms, a cycloalkoxycarbonyl group having a total of 6 to 8 carbon atoms or an $R_1$—CO—O—($R_2$CH)—O—CO— group, in which $R_1$ is an alkyl group having 1 to 5 carbon atoms, a cycloalkyl group having 5 to 7 carbon atoms, a phenylalkyl group, an alkoxy group having 1 to 5 carbon atoms, a cycloalkoxy group having 5 to 7 carbon atoms or a phenyl group and $R_2$ is a hydrogen atom, an alkyl group having 1 to 4 carbon atoms, a cycloalkyl group having 5 to 7 carbon atoms or a phenyl group, and additionally in the 6- or 7-membered azacycloalkyl groups thus formed a >CH— unit in the 4-position can be replaced by a nitrogen atom or in the 5- to 7-membered azacycloalkyl groups thus formed a —CH$_2$—CH< unit can be replaced by a —CH=C< unit and in the piperazinyl or homopiperazinyl rings thus formed one or two methylene groups, which are adjacent to the nitrogen atom in the 4-position, can in each case be replaced by a carbonyl group, or a quinuclidinyl group, B is a straight-chain or branched alkylene group having 1 to 8 carbon atoms, an alkenylene group having 2 or 3 carbon atoms, an —O(CH$_2$)$_n$—, —(CH$_2$)$_n$O—, —S(CH$_2$)$_n$—, —(CH$_2$)$_n$S—, —CONR$_3$—, —R$_3$NCO—, —NR$_3$(CH$_2$)$_n$— or —(CH$_2$)$_n$NR$_3$— group, in which n is the number 1 or 2 and $R_3$ is a hydrogen atom, a phenylalkyl group which is optionally substituted in the phenyl nucleus by a fluorine, chlorine or bromine atom or by an alkyl, hydroxyl or alkoxy group, or is an alkyl or pyridylalkyl group, and an oxygen, sulphur or nitrogen atom of the radical B is not directly bonded to a nitrogen atom of the radical A or to a nitrogen atom of the 5-membered heterocycle, or a bond, with the proviso that a nitrogen atom of the group A is not bonded to a nitrogen atom of the 5-membered heterocycle, a second of the radicals $X_1$ to $X_5$, is a group of the formula

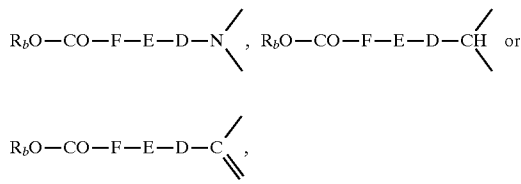

in which

D is a —CO—, —CO—NR$_3$—, —NR$_3$—CO—, —SO$_2$—NR$_3$—, —NR$_3$—SO$_2$—, —W—CO—NR$_3$—, —W$_1$—NR$_3$—CO—, —W$_1$—SO$_2$NR$_3$—, —W$_1$—NR$_3$SO$_2$—, —CO—NR$_3$—W$_1$—, —NR$_3$—CO—W$_1$—, —SO$_2$NR$_3$—W$_1$—, —NR$_3$SO$_2$—W$_1$—, —CO—(CH$_2$)$_n$—O—, —CO—(CH$_2$)$_n$—NR$_3$—, —O—W$_1$—, —W$_1$—O—, —S—W$_1$—, —W$_1$—S—, —NR$_3$—W$_1$—, —W$_1$NR$_3$—, —(CH$_2$)$_n$—O—(CH$_2$)$_n$—, —(CH$_2$)$_n$—NR$_3$—(CH$_2$)$_n$— or —W— group or alternatively a —W—CO— group if the 5-membered $X_1$ to $X_5$ ring is not an isoxazole or isoxazoline ring, with the proviso that the above groups are not bonded to a nitrogen atom of the 5-membered heterocycle via a carbonyl or sulphonyl group, in which $R_3$ and n are defined as mentioned above, $W_1$ is an alkylene group having 1 to 3 carbon atoms, $W_2$ is an alkenylene group having 2 or 3 carbon atoms and W is an alkylene group having 1 to 3 carbon atoms or an alkenylene group having 2 or 3 carbon atoms, E is a phenylene group which can be mono- or disubstituted by fluorine, chlorine or bromine atoms, or by alkyl, trifluoromethyl, R$_3$O— or R$_3$O—CO—CH$_2$—O— groups, it being possible for the substituents to be identical or different and R$_3$ being defined as mentioned above.

a pyridinylene, pyrimidinylene, pyrazinylene, pyridazinylene or triazinylene group, each of which can be substituted in the carbon ring system by a chlorine atom or by an alkyl or alkoxy group, it additionally being possible for one or two —CH=N— groups each to be replaced by a —CO—NR$_3$— group, in which R$_3$ is defined as mentioned above, and one of the nitrogen atoms can also be bonded to the radical F, instead of to the radical R$_3$, if this is not a bond, a cycloalkylene group having 4 to 5 carbon atoms, which is optionally substituted by an alkyl, phenylalkyl or phenyl group, in which a >CH— unit can be replaced by a nitrogen atom and additionally a methylene group adjacent to the nitrogen atom can be replaced by a carbonyl group, or a cycloalkylene group having 6 or 7 carbon atoms, which is optionally substituted by an alkyl, phenylalkyl or phenyl group, in which one or two >CH— units can each be replaced by a nitrogen atom, it additionally being possible for a methylene group adjacent to a nitrogen atom to be replaced by a carbonyl group, F is a bond, a straight-chain or branched alkylene or alkenylene group, which is optionally substituted by a phenylalkyl, phenyl, pyridyl, $R_3O$—, $R_3S$—, $R_3R_3N$—, $R_3O$—CO—, $R_3R_3N$—CO—, $R_4CO$—$NR_3$—, $R_5O$—CO—$NR_3$—, $R_4SO_2$—$NR_3$—, $R_3R_3N$—CO—$NR_3$—, $R_3O$—CO—$C_{1-3}$-alkyl or $R_3R_3N$—CO—$C_{1-3}$-alkyl group, in which in each case the alkylene moiety can contain 1 to 5 carbon atoms and the alkenylene moiety can contain 2 to 5 carbon atoms, or a —Y—$W_1$— group, in which $R_3$ and $W_1$ are defined as mentioned above, $R_4$ is an alkyl group having 1 to 5 carbon atoms, or a phenylalkyl, phenyl or pyridyl group, $R_5$ is an alkyl group having 1 to 5 carbon atoms, a phenylalkyl, cycloalkyl or cycloalkylalkyl group and Y is an oxygen atom, a —CO—, sulphenyl-, sulphinyl-, sulphonyl-, —$NR_3$—, —$N(COR_4)$—, —$N(SO_2R_4)$—, —CO—$NR_3$— or —$NR_3$—CO— group, Y being linked to the radical E, with the proviso that a heteroatom of the radical E is not bonded to a nitrogen or sulphur atom of the above groups, and $R_b$ is an alkyl group having 1 to 5 carbon atoms or a cycloalkyl group having 5 to 7 carbon atoms in the cycloalkyl moiety, it being possible for the above-mentioned groups each to be substituted in the alkyl and cycloalkyl moiety from position 2 by an $R_3O$— or $R_3R_3N$— group, or is an alkenyl group having 3 to 5 carbon atoms, a phenylalkyl group, a cycloalkylalkyl group having 3 to 7 carbon atoms in the cycloalkyl moiety, which can be substituted in the alkyl moiety from position 2 by an $R_3O$— or $R_3R_3N$— group, $R_3$ in each case being defined as mentioned above, an $R_1$—CO—O—($R_2$CH)— group, in which $R_1$ and $R_2$ are defined as mentioned above, or alternatively a hydrogen atom if the $R_b$O—CO— group is not directly bonded to a nitrogen atom of the radical E, the distance between the furthest removed nitrogen atom of the group A and the $COOR_b$ group being at least 11 bonds and the above-mentioned A—B— and $R_b$O—CO—F—E—D— groups being in the 1,3-position relative to one another, a third of the radicals $X_1$ or $X_5$ is a sulphur atom, an

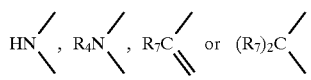

group or an N atom, $R_4$ being as defined at the outset and $R_7$ being a hydrogen atom, or an alkyl, phenylalkyl or phenyl group, a fourth of the radicals $X_1$ to $X_5$ is an oxygen, sulphur or nitrogen atom, or an

group, in which $R_7$ is defined as mentioned above, a fifth of the radicals $X_1$ to $X_5$ is a nitrogen atom, an

or $(R_7)_2C<$ group, $R_7$ being defined as mentioned above, or alternatively two adjacent radicals of the radicals $X_1$ to $X_5$ together are an o-phenylene group, but at least one of the radicals $X_1$ to $X_5$ in the above-mentioned $X_1$–$X_5$-ring having to be a ring heteroatom, where, if nothing different has been mentioned, the above-mentioned alkyl, alkylene or alkoxy moieties can each contain 1 to 3 carbon atoms and the above-mentioned cycloalkyl moieties can each contain 3 to 7 carbon atoms.

The above-mentioned general formula I thus includes, for example, the appropriately substituted furan, tetrahydrofuran, 2,3-dihydrofuran, 2,5-dihydrofuran, thiophene, 2,3-dihydrothiophene, 2,5-dihydrothiophene, tetrahydrothiophene, pyrrole, indole, isoindole, 2,3-dihydroindole, 2,3-dihydroisoindole, imidazole, 4,5-dihydroimidazole, tetrahydroimidazole, benzimidazoline, pyrazole, 4,5-dihydropyrazole, 2,3-dihydropyrazole, indazole, 2,3-dihydroindazole, oxazole, isoxazole, oxazoline, oxazolidine, isoxazoline, thiazole, isothiazole, thiazoline, thiazolidine, 1,3,4-oxadiazole, 1,2,4-oxadiazole, 1,3,4-thiadiazole, 1,2,4-thiadiazole, 1,2,3-triazole, 1,2,4-triazole and tetrazole derivatives.

Preferred compounds of the general formula I, however, are those in which one of the radicals $X_1$ to $X_5$ is a group of the formula

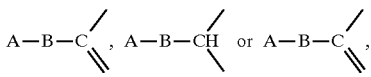

in which

A is a cycloalkyl group having 5 to 7 carbon atoms, which is optionally substituted by 1 to 4 alkyl groups, in which an unsubstituted methylene group is replaced by the $R_a$—N< group, which can additionally be substituted by a cyano, aminocarbonyl, carboxyl or alkoxycarbonyl group or alternatively, if the substitution does not take place in the α-position relative to a nitrogen atom, by a hydroxyl or alkoxy group, and in which $R_a$ is a hydrogen atom, an alkyl, phenylalkyl, alkoxycarbonyl or phenylalkoxycarbonyl group or an $R_1$—CO—O—($R_2$CH)—O—CO— group, in which $R_1$ is an alkyl, cycloalkyl, phenyl, alkoxy or cycloalkoxy group each having 5 to 7 carbon atoms in the cycloalkyl moiety and $R_2$ is a hydrogen atom or a methyl group, and additionally in the 6- or 7-membered azacycloalkyl groups thus formed a >CH— unit in the 4-position can be replaced by a nitrogen atom or in the 5- to 7-membered azacycloalkyl groups thus formed a —$CH_2$—CH< unit can be replaced by a —CH=C< unit, or a quinuclidinyl group, B is an alkylene group having 1 to 5 carbon atoms, an alkenylene group having 2 or 3 carbon atoms, or an —OCH$_2$—, —CH$_2$O—, —SCH$_2$—, —CH$_2$S—, —CONR$_3$—, —R$_3$NCO—, —NR$_3$CH$_2$— or —CH$_2$NR$_3$— group, in which R$_3$ is a hydrogen atom, or an alkyl, phenylalkyl or pyridylalkyl group, and an oxygen, sulphur or nitrogen atom of the radical B is not bonded directly to a nitrogen atom of the radical A or to a nitrogen atom of the 5-membered heterocycle, or a bond, with the proviso that a nitrogen atom of the group A is not bonded to a nitrogen atom of the 5-membered heterocycle, a second of the radicals X$_1$ to X$_5$ is a group of the formula

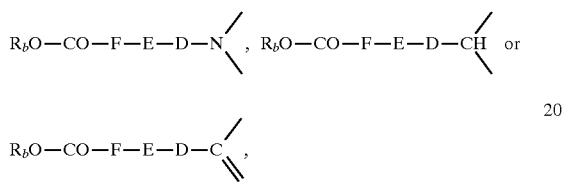

in which

D is a —CO—, —CO—NR$_3$—, —NR$_3$—CO—, —SO$_2$—NR$_3$—, —NR$_3$—SO$_2$—, —W—CO—NR$_3$—, —W$_1$—NR$_3$—CO—, —W$_1$—SO$_2$NR$_3$—, —W$_1$—NR$_3$SO$_2$—, —CO—NR$_3$—W$_1$—, —NR$_3$CO—W$_1$—, —SO$_2$NR$_3$—W$_1$—, —NR$_3$SO$_2$—W$_1$—, —CO—CH$_2$—O—, —CO—CH$_2$—NR$_3$—, —O—W$_1$—, —W$_1$—O—, —S—W$_1$—, —W$_1$—S—, —NR$_3$—W$_1$—, —W$_1$—NR$_3$—, —CH$_2$—O—CH$_2$—, —CH$_2$—NR$_3$—CH$_2$— or —W$_1$— group or alternatively a —W—CO— group, if the 5-membered X$_1$ to X$_5$ring is not an isoxazole or isoxazoline ring, with the proviso that the above groups are not bonded to a nitrogen atom of the 5-membered heterocycle via a carbonyl or sulphonyl group, in which R$_3$ is defined as mentioned above,
W$_1$ is an alkylene group having 1 to 3 carbon atoms,
W$_2$ is an alkenylene group having 2 or 3 carbon atoms, and
W is an alkylene group having 1 to 3 carbon atoms or an alkenylene group having 2 or 3 carbon atoms, E is a phenylene group which can be substituted by a fluorine, chlorine or bromine atom, or by an alkyl, trifluoromethyl, R$_3$O— or R$_3$O—CO—CH$_2$—O— group, R$_3$ being defined as mentioned above, a pyridinylene, pyrimidinylene, pyrazinylene or pyridazinylene group, each of which can be substituted in the carbon ring system by an alkyl or alkoxy group, a 1,4-cyclohexylene group, in which one or two >CH— units can each be replaced by a nitrogen atom, it additionally being possible in each case for a methylene group adjacent to a nitrogen atom to be replaced by a carbonyl group, a 1,3-cyclohexylene group, in which a >CH— unit can be replaced by a nitrogen atom, it then additionally being possible for a methylene group adjacent to the nitrogen atom to be replaced by a carbonyl group, a 1,3-pyrrolidinylene, 2-oxo-1,3-pyrrolidinylene, 5-oxo-1,3-pyrrolidinylene or 1,4-homopiperazinylene, F is a bond, a straight-chain or branched alkylene group having 1 to 5 carbon atoms, which is optionally substituted by a phenyl, pyridyl, R$_3$O—, R$_4$CO—NR$_3$—, R$_5$O—CO—NR$_3$—, R$_4$SO$_2$—NR$_3$— or R$_3$R$_3$N—CO—NR$_3$— group, or a —Y—W$_1$— group, in which R$_3$ and W$_1$ are defined as mentioned above,
R$_4$ is an alkyl group having 1 to 5 carbon atoms, or a phenylalkyl, phenyl or pyridyl group,
R$_5$ is an alkyl group having 1 to 5 carbon atoms or a phenylalkyl group and
Y is an oxygen atom, a sulphenyl, —NR$_3$—, —N(COR$_4$)— or —N(SO$_2$R$_4$)— group, Y being linked to the radical E, with the proviso that a heteroatom of the radical E is not bonded to a nitrogen or sulphur atom of the above groups, and R$_b$ is an alkyl group having 1 to 5 carbon atoms or a cycloalkyl group having 5 to 7 carbon atoms in the cycloalkyl moiety, each of which can be substituted in the alkyl and cycloalkyl moiety from position 2 by an R$_3$O— or R$_3$R$_3$N— group, or is an alkenyl group having 3 to 5 carbon atoms, a phenylalkyl group, a cycloalkylalkyl group having 3 to 7 carbon atoms in the cycloalkyl moiety, which can be substituted in the alkyl moiety from position 2 by an R$_3$O— or R$_3$R$_3$N— group, R$_3$ in each case being defined as mentioned above, an R$_1$—CO—O—(R$_2$CH)— group, in which R$_1$ and R$_2$ are defined as mentioned above, or alternatively a hydrogen atom if the R$_b$O—CO— group is not directly bonded to a nitrogen atom of the radical E, the distance between the furthest removed nitrogen atom of the group A and the COOR$_b$ group being at least 11 bonds, and the above-mentioned A—B— and R$_b$O—CO—F—E—D— groups being in the 1,3-position relative to one another, a third of the radicals X$_1$ to X$_5$ is a sulphur atom, an

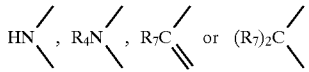

group or an N atom,
R$_4$ being as defined at the outset and
R$_7$ being a hydrogen atom, or an alkyl, phenylalkyl or phenyl group, a fourth of the radicals X$_1$ to X$_5$ is an oxygen, sulphur or nitrogen atom or an

group, in which R$_7$ is defined as mentioned above,
a fifth of the radicals X$_1$ to X$_5$ is a nitrogen atom, an

or (R$_7$)$_2$C< group, R$_7$ being defined as mentioned above,
or alternatively two adjacent radicals of the radicals X$_1$ to X$_5$ together are an o-phenylene group, but at least one of the radicals X$_1$ to X$_5$ in the above-mentioned X$_1$–X$_5$-ring having to be a ring heteroatom, where, if nothing different has been mentioned,
the above-mentioned alkyl, alkylene or alkoxy moieties can each contain 1 to 3 carbon atoms, tautomers thereof, stereoisomers thereof including mixtures thereof and salts thereof, in particular physiologically tolerated salts thereof with inorganic or organic acids or bases.

Particularly preferred compounds of the general formula I, however, are those in which one of the radicals $X_1$ to $X_5$ is a group of the formula

in which

A is a cycloalkyl group having 5 or 6 carbon atoms, in which an unsubstituted methylene group in the 3- or 4-position is replaced by the $R_a$—N< group, in which $R_a$ is a hydrogen atom, or a $C_{1-2}$-alkyl, $C_{1-4}$-alkoxycarbonyl or benzyloxycarbonyl group, and additionally in the 4-piperidinyl groups thus formed a >CH— unit in the 4-position can be replaced by a nitrogen atom, B is a bond, or a $C_{1-2}$-alkylene, —OCH$_2$— or —CH$_2$O— group, a second of the radicals $X_1$ to $X_5$ is a group of the formula

in which

D is a —CO—, —CO—NR$_3$—, —NR$_3$—CO—, —W—CO—NR$_3$—, —CO—NR$_3$—W$_1$—, —NR$_3$—CO—W$_1$—, —CO—CH$_2$—O—, —O—W$_1$—, —W$_1$—O— or —W$_1$— group or alternatively a —W—CO— group, if the 5-membered $X_1$ to $X_5$ ring is not an isoxazole ring, with the proviso that the above groups are not bonded to a nitrogen atom of the 5-membered heterocycle via a carbonyl group, in which $R_3$ is a hydrogen atom, or a $C_{1-4}$-alkyl, benzyl or pyridylmethyl group, $W_1$ is a $C_{1-2}$-alkylene group and W is a $C_{1-2}$-alkylene or vinylene group, E is a 1,4-phenylene group which can be substituted by a hydroxyl, methoxy, carboxymethoxy or methoxycarbonylmethoxy group, a 1,4-cyclohexylene group in which one or two >C— units can each be replaced by a nitrogen atom, F is a bond, a straight-chain or branched alkylene group having 1 to 3 carbon atoms, which is optionally substituted by an $R_4CO$—NR$_3$— or $R_4SO_2$—NR$_3$— group, or a —Y—W$_1$— group, in which $R_3$ and $W_1$ are defined as mentioned above, $R_4$ is a methyl, ethyl or phenyl group and Y is an oxygen atom, or an —NR$_3$— or —N(SO$_2$R$_4$)— group, Y being linked to the radical E, with the proviso that a nitrogen atom of the radical E is not bonded to a nitrogen atom of the above groups, and $R_3$ and $R_4$ are defined as mentioned above, and $R_b$ is a $C_{1-5}$-alkyl, cyclohexyl or benzyl group or alternatively a hydrogen atom if the $R_bO$—CO— group is not directly bonded to a nitrogen atom of the radical E, the distance between the furthest removed nitrogen atom of the group A and the COOR$_b$ group being at least 11 bonds and the above-mentioned A—B— and $R_bO$—CO—F—E—D— groups being in the 1,3-position relative to one another, a third of the radicals $X_1$ to $X_5$ is an HN<, $R_4$N< or

group or a nitrogen atom, $R_4$ being as defined at the outset and $R_7$ being a hydrogen atom, or a $C_{1-2}$-alkyl or phenyl group, a fourth of the radicals $X_1$ to $X_5$ is an oxygen, sulphur or nitrogen atom or a

group, in which $R_7$ is defined as mentioned above, a fifth of the radicals $X_1$ to $X_5$ is a nitrogen atom or an

group, $R_7$ being defined as mentioned above and at least one of the radicals $X_1$ to $X_5$ in the above-mentioned $X_1$–$X_5$ ring having to be a ring heteroatom, tautomers thereof, stereoisomers thereof including mixtures thereof and salts thereof, in particular physiologically tolerated salts thereof with inorganic or organic acids or bases.

Very particularly preferred compounds of the general formula I, however, are those in which one of the radicals $X_1$ to $X_5$ is a group of the formula

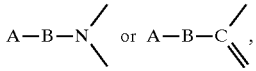

in which

A is a cyclohexyl group, in which an unsubstituted methylene group in the 4-position is replaced by the $R_a$—N< group, in which $R_a$ is a is a hydrogen atom, or a $C_{1-4}$-alkoxycarbonyl or benzyloxycarbonyl group, B is a bond or a $C_{1-2}$-alkylene group, a second of the radicals $X_1$ to $X_5$ is a group of the formula

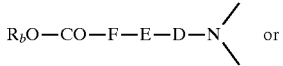
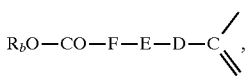

in which

D is a —CH$_2$CH$_2$—, —CO—, —CH$_2$—O—, —CH$_2$CH$_2$—CO—, —CH=CH—CO—, —CO—NR$_3$—, —NR$_3$—CO—, —CH$_2$CH$_2$—CO—NR$_3$—, —CO—NR$_3$—CH$_2$— or —CO—NR$_3$—CH$_2$CH$_2$— group, with the proviso that the above groups are not bonded to a nitrogen atom of the 5-membered heterocycle via a carbonyl group, in which R$_3$ is a hydrogen atom or a pyridylmethyl group, E is a 1,4-phenylene, 1,4-cyclohexylene, 1,4-piperidinylene or 1,4-piperazinylene group, F is a bond, or a —CH$_2$—, —CH$_2$CH$_2$—, —O—CH$_2$—, —O—CH$_2$CH$_2$— or —N(SO$_2$CH$_3$)—CH$_2$— group, and R$_b$ is a C$_{1-4}$-alkyl or cyclohexyl group or alternatively a hydrogen atom if the R$_b$O—CO— group is not directly bonded to a nitrogen atom of the radical E, the distance between the furthest removed nitrogen atom of the group A and the COOR$_b$ group being at least 11 bonds and the above-mentioned A—B— and R$_b$O—CO—F—E—D— groups being in the 1,3-position relative to one another, a third of the radicals X$_1$ to X$_5$ is a nitrogen atom or an

group, in which

R$_7$ is a hydrogen atom or a methyl group, a fourth of the radicals X$_1$ to X$_5$ is a sulphur or nitrogen atom or an

group, in which R$_7$ is defined as mentioned above, a fifth of the radicals X$_1$ to X$_5$ is a nitrogen atom or an

group, R$_7$ being defined as mentioned above and at least one of the radicals X$_1$ to X$_5$ in the above-mentioned X$_1$–X$_5$ ring having to be a ring heteroatom, tautomers thereof, stereoisomers thereof including mixtures thereof and salts thereof, in particular physiologically tolerable salts thereof with inorganic or organic acids or bases.

Particularly preferred compounds which may be mentioned by way of example are the following:

(1) 4-[[trans-4-(2-carboxyethyl)cyclohexyl]aminocarbonyl]-1-(4-piperidyl)imidazole, (2) 5-[[trans-4-(2-carboxyethyl)cyclohexyl]aminocarbonyl]-4-methyl-2-(4-piperidyl)-1,3-thiazole, (3) 5-[[4-(carboxymethoxy)phenyl]aminocarbonyl]-4-methyl-2-(4-piperidyl)-1,3-thiazole, (4) 5-[[trans-4-(2-carboxyethyl)cyclohexyl]aminocarbonyl]-2-(4-piperidyl)-1,3,4-thiadiazole, (5) 5-[[4-(carboxymethoxy)phenyl]aminocarbonyl]-2-(4-piperidyl)-1,3,4-thiadiazole, (6) 5-[[trans-4-(carboxymethoxy)cyclohexyl]aminocarbonyl]-2-(4-piperidyl)-1,3-thiazole, (7) 5-[[4-(carboxymethoxy)phenyl]aminocarbonyl]-2-(4-piperidyl)-1,3-thiazole, (8) 5-[[trans-4-(2-carboxyethyl)cyclohexyl]aminocarbonyl]-2-(4-piperidyl)-1,3-thiazole, (9) 4-[[trans-4-carboxycyclohexyl]aminocarbonyl]-1-[2-(4-piperidyl)ethyl]imidazole, C$_{1-4}$-alkyl and cyclohexyl esters thereof and salts thereof.

According to the invention, the novel compounds are obtained, for example, by the following processes:

a) to prepare a compound of the general formula I in which R$_a$ is a hydrogen atom and R$_b$, with the exception of the R$_1$—CO—O—(R$_2$CH)— group, has the meanings mentioned for R$_b$ at the outset, R$_a$ has the meanings mentioned for R$_a$ at the outset and R$_b$ is a hydrogen atom or R$_a$ and R$_b$ are each a hydrogen atom: conversion of a compound of the general formula

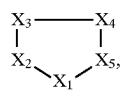

in which one of the radicals X$_1$ to X$_5$ is a group of the formula

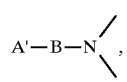

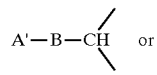

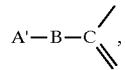

in which

B is as defined at the outset and

A' has the meanings mentioned for A at the outset and additionally contains a removable protective radical for an imino group, a second of the radicals X$_1$ to X$_5$ is a group of the formula

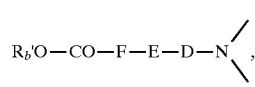

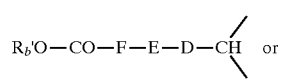

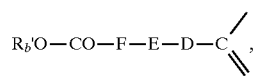

in which

F, E and D are as defined at the outset and

R$_b$' has the meanings mentioned for R$_b$ at the outset and is additionally a removable protective radical for a hydroxyl group of a carboxyl group, but where at least one of the radicals A' or R$_b$' contains or has to be a removable protective radical, and the remainder of the radicals X$_1$ to X$_5$ are as defined at the outset, by means of hydrolysis, treatment with an acid or base, thermolysis or hydrogenolysis into a compound of the general formula I, in which $R_a$ is a hydrogen atom and $R_b$, with the exception of the $R_1$—CO—O—$(R_2CH)$— group, has the meanings mentioned for $R_b$ at the outset, $R_a$ has the meanings mentioned for $R_a$ at the outset and $R_b$ is a hydrogen atom or $R_a$ and $R_b$ are each a hydrogen atom.

As protective groups for an imino group, for example, acyl groups such as the formyl, acetyl, trifluoroacetyl or benzoyl group and carbonic acid ester radicals such as the allyloxycarbonyl, ethoxycarbonyl, tert-butoxycarbonyl or benzyloxycarbonyl group can be removed by means of hydrolysis, arylmethyl groups such as the benzyl group or arylmethoxycarbonyl groups such as the benzyloxycarbonyl group can be removed by means of hydrogenolysis and carbonic acid ester radicals with tertiary alcohols such as the tert-butoxycarbonyl group can be removed by means of treatment with an acid or thermolysis, and as protective groups for a hydroxyl group of a carboxyl group, for example, the functional derivatives of a carboxyl group such as its unsubstituted or substituted amides, esters, thioesters, trimethylsilyl esters, ortho esters or imino esters can be converted by means of hydrolysis into a carboxyl group, esters with tertiary alcohols, e.g. the tert-butyl esters, can be converted by means of treatment with an acid or thermolysis into a carboxyl group and esters with aralkanols, e.g. the benzyl ester, can be converted by means of hydrogenolysis into a carboxyl group.

The hydrolysis is expediently carried out either in the presence of an acid such as hydrochloric acid, sulphuric acid, phosphoric acid, acetic acid, trichloroacetic acid, trifluoroacetic acid or mixtures thereof or in the presence of a base such as lithium hydroxide, sodium hydroxide or potassium hydroxide in a suitable solvent such as water, methanol, ethanol, isopropanol, ether, tetrahydrofuran, dioxane, methylene chloride or mixtures thereof at temperatures between $-10°$ and $120°$ C., e.g. at temperatures between $0°$ C. and the boiling point of the reaction mixture, the hydrogenolysis is expediently carried out with hydrogen in the presence of a catalyst such as palladium/carbon in a solvent such as methanol, ethanol, ethyl acetate, tetrahydrofuran, glacial acetic acid or trifluoroacetic acid, if appropriate with addition of an acid such as hydrochloric acid, at temperatures between $0°$ and $100°$ C., but preferably at temperatures between $20°$ and $60°$ C., and at a hydrogen pressure of 1 to 7 bar, but preferably of 3 to 5 bar, the thermolysis is expediently carried out by heating, if appropriate in the presence of an acid such as trifluoroacetic acid and the treatment with an acid is expediently carried out in the presence of an acid such as trifluoroacetic acid, hydrogen bromide/glacial acetic acid or hydrogen chloride, if appropriate using a solvent such as methylene chloride, tetrahydrofuran, dioxane, methanol, ethanol, ether or mixtures thereof.

To prepare a compound of the general formula I in which $R_a$ is a hydrogen atom and $R_b$, with the exception of the $R_1$—CO—O—$(R_2CH)$— group, is as defined at the outset, a corresponding compound of the general formula II in which A' contains a benzyloxycarbonyl group and $R_b'$ is defined as mentioned above, is preferably converted into the desired compound by means of hydrogen bromide/glacial acetic acid at room temperature or a corresponding compound of the general formula II in which A' contains a tert-butoxycarbonyl group and $R_b'$ is defined as mentioned above is converted into the desired compound by means of trifluoroacetic acid/methylene chloride at room temperature or a corresponding compound of the general formula II in which A' contains a tert-butoxycarbonyl group and $R_b'$ is an alkyl group is converted into the desired compound by means of hydrogen chloride in an appropriate alkanol, e.g. in methanol, methanol/ether or methanol/dioxane/ether at room temperature, or to prepare a compound of the general formula I in which $R_a$ is a hydrogen atom or a $C_{1-3}$-alkyl or phenyl-$C_{1-3}$-alkyl group and $R_b$ is a hydrogen atom, preferably an appropriate compound of the general formula II in which A' has the meanings mentioned for A at the outset and $R_b'$ is defined as mentioned above is converted into the desired compound by means of an acid such as hydrochloric acid or by means of a base such as sodium hydroxide or lithium hydroxide in a solvent such as methanol, tetrahydrofuran, water or mixtures thereof at temperatures between $0°$ C. and the boiling point of the solvent employed, but preferably at temperatures between $0°$ and $40°$ C., or an appropriate compound of the general formula II in which A' contains a benzyloxycarbonyl group and $R_b'$ is a tert-butyl group is converted into the desired compound by means of an acid such as hydrogen bromide/glacial acetic acid at temperatures between $0°$ C. and the boiling point of the solvent employed, but preferably at temperatures between $0°$ and $40°$ C.

If, for example, $R_b'$ in a compound of the formula II is the tert-butyl group and/or $R_a$ is the tert-butoxycarbonyl group, these groups are particularly advantageously removed by treatment with an acid such as trifluoroacetic acid, formic acid, acetic acid, p-toluenesulphonic acid, sulphuric acid, hydrochloric acid, hydrogen bromide, phosphoric acid or polyphosporic acid, if appropriate in a solvent such as methylene chloride, chloroform, benzene, toluene, diethyl ether, tetrahydrofuran, dioxane, methanol, ethanol or mixtures thereof, preferably at temperatures between $-10°$ and $120°$ C., e.g. at temperatures between $0°$ and $60°$ C., or alternatively thermally, if appropriate in an inert solvent such as methylene chloride, chloroform, benzene, toluene, tetrahydrofuran or dioxane and preferably in the presence of a catalytic amount of an acid such as p-toluenesulphonic acid, sulphuric acid, phosphoric acid or polyphosphoric acid, preferably at the boiling point of the solvent used, e.g. at temperatures between $40°$ and $120°$ C.

If, for example, in a compound of the general formula II $R_a$ is a benzyl or benzyloxycarbonyl group and $R_b$ is a benzyl group, these protective groups are particularly advantageously removed hydrogenolytically with hydrogen in the presence of a hydrogenation catalyst such as palladium/carbon in a suitable solvent such as methanol, ethanol, ethanol/water, glacial acetic acid, ethyl acetate, dioxane or dimethylformamide, preferably at temperatures between $0°$ and $50°$ C., e.g. at room temperature, and a hydrogen pressure of 1 to 5 bar.

If a hydrobromide is employed as the starting compound in the ester hydrolysis by means of hydrochloric acid, after the evaporation of the hydrochloric acid and on recrystallization after the evaporation of the hydrochloric acid the corresponding hydrobromide is preferably obtained.

b) to prepare a compound of the general formula I in which four of the radicals $X_1$ to $X_5$ are as defined at the outset and the last radical of the radicals $X_1$ to $X_5$ is an $R_bO$—CO—
F—E—D—CH<, $R_b$—CO—F—E—D—N< or

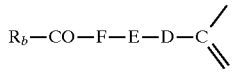

group in which

D is a —CO—$NR_3$—, —$NR_3$—CO—, —$SO_2$—$NR_3$—, —$NR_3$—$SO_2$—, —W—CO—$NR_3$—, —$W_1$—$NR_3$—CO—, —$W_1$—$SO_2NR_3$—, —$W_1NR_3SO_2$—, —CO—$NR_3$—$W_1$—, —$NR_3$—CO—$W_1$—, —$SO_2NR_3$—$W_1$— or —$NR_3SO_2$—$W_1$— group or D together with the hydrogen atom of an imino group present in the radical E is a —CO— or —W—CO— group:

reaction of a compound of the general formula

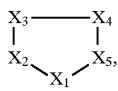 (III)

with a compound of the general formula $U_1$—E—F—CO—$OR_b$, (IV)

in which

E, F, $R_b$, with the exception of the $R_1$—CO—O—$(R_2CH)$—O—CO— group, and four of the radicals $X_1$ to $X_5$ are as defined at the outset, the last of the radicals $X_1$ to $X_5$ is a $Z_1$—CO—, $Z_1$—$SO_2$—, $Z_1$—CO—W— or $Z_1SO_2$—$W_1$— group and $U_1$ is a hydrogen atom of an imino group of the radical E, or an $HNR_3$— or $HNR_3$—$W_1$— group or the last of the radicals $X_1$ to $X_5$ is an $HNR_3$— or $HNR_3$—$W_1$— group and $U_1$ is a $Z_2$—CO—, $Z_2$—$SO_2$—, $Z_2$—CO—$W_1$— or $Z_2$—$SO_2$—$W_1$— group, in which $R_3$, W and $W_1$ are as defined at the outset, $Z_1$ or $Z_2$ is a nucleofugic leaving group such as a hydroxyl group, a halogen atom, e.g. a chlorine or bromine atom, or an imidazolyl, 4-nitrophenoxy or benzotriazol-1-oxy group.

The reaction is expediently carried out in a solvent such as methylene chloride, dimethylformamide, dimethyl sulphoxide, benzene, toluene, chlorobenzene, tetrahydrofuran, dioxane or mixtures thereof, if appropriate in the presence of a dehydrating agent, e.g. in the presence of isobutyl chloroformate, thionyl chloride, trimethylchlorosilane, hydrochloric acid, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide, 2-(1H-benzotriazol-1-yl)-1,1,3,3-tetramethyluronium salts such as 2-(1H-benzo-triazol-1-yl)-1,1,3,3-tetramethyluronium tetrafluoroborate, N,N'-thionyldiimidazole, N,N'-carbonyldiimidazole or triphenylphosphine/carbon tetrachloride, if appropriate in the presence of 4-dimethylaminopyridine or 1-hydroxybenzo-triazole and/or of a base such as triethylamine, N-ethyldiisopropylamine, N-methylmorpholine or pyridine, at temperatures between 0° and 150° C., preferably at temperatures between 0° and 100° C.

The sulphonamides of the general formula I, however, are obtained particularly advantageously by reaction of a corresponding sulphonyl halide, preferably the chloride, optionally prepared in the reaction mixture with an appropriate amine.

c) to prepare a compound of the general formula I in which D is a —$CH_2CH_2$—CO—$NR_3$— or —$CH_2CH_2CH_2$—CO—$NR_3$— group:

catalytic hydrogenation of a compound of the general formula

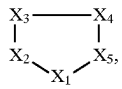 (V)

in which $X_1$ to $X_5$ are as defined at the outset, with the proviso that D in the second of the radicals $X_1$ to $X_5$ contains an alkenylene group having 2 or 3 carbon atoms.

The catalytic hydrogenation is preferably carried out in a solvent such as water, methanol, ethanol, tetrahydrofuran, dioxane or mixtures thereof at temperatures between 0° and 100° C., preferably at temperatures between 20° C. and the boiling point of the solvent used, with hydrogen in the presence of a hydrogenation catalyst, e.g. in the presence of palladium/carbon, at a hydrogen pressure of 1 to 5 bar.

d) to prepare a compound of the general formula I in which $R_b$ is an alkyl group having 1 to 5 carbon atoms, an alkenyl group having 3 to 5 carbon atoms, a phenylalkyl group, a cycloalkyl or cycloalkylalkyl group each having 5 to 7 carbon atoms in the cycloalkyl moiety or an $R_1$—CO—C—$(R_2CH)$— group:

reaction of a compound of the general formula

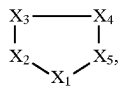 (VI)

in which $X_1$ to $X_5$, with the proviso as defined at the outset that $R_b$ is a hydrogen atom, with a compound of the general formula HO—$R_b$, (VII)

or with a compound of the general formula $Z_3$—$R_c$, (VIII)

in which $R_b$ is an alkyl group having 1 to 5 carbon atoms, an alkenyl group having 3 to 5 carbon atoms, a phenylalkyl group or a cycloalkyl or cycloalkylalkyl group each having 5 to 7 carbon atoms in the cycloalkyl moiety, $R_c$ is an alkyl group having 1 to 5 carbon atoms, an alkenyl group having 3 to 5 carbon atoms, a phenylalkyl group, a cycloalkyl or cycloalkylalkyl group each having 5 to 7 carbon atoms in the cycloalkyl moiety or an $R_1$—CO—O—$(R_2CH)$— group, in which $R_1$ and $R_2$ are as defined at the outset, and $Z_3$ is a leaving group such as a halogen atom, e.g. a chlorine or bromine atom.

The reaction with an alcohol of the general formula VII is expediently carried out in a solvent such as methylene chloride, benzene, toluene, chlorobenzene, ether, tetrahydrofuran, dioxane or mixtures thereof, but preferably in an alcohol of the general formula VII, if appropriate in the presence of an acid such as hydrochloric acid, sulphuric acid, methanesulphonic acid or p-toluenesulphonic acid, or in the presence of a dehydrating agent, e.g. in the presence of isobutyl chloroformate, thionyl chloride, trimethylchlorosilane, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole, N,N'-thionyldiimidazole, triphenylphosphine/carbon tetrachloride or triphenylphosphine/diethyl azodicarboxylate, if appropriate in the presence of a base such as potassium carbonate, N-ethyldiisopropylamine or N,N-dimethyl-aminopyridine, expediently at temperatures between 0° and 150° C., preferably at temperatures between 0° and 80° C.

With a compound of the general formula VIII, the reaction is expediently carried out in a solvent such as methylene chloride, tetrahydrofuran, dioxane, dimethyl sulphoxide, dimethylformamide or acetone, if appropriate in the presence of a reaction accelerator such as sodium or potassium iodide and preferably in the presence of a base such as sodium carbonate or potassium carbonate or in the presence of a tertiary organic base such as N-ethyldiisopropylamine or N-methylmorpholine, which at the same time can also be used as a solvent, or if appropriate in the presence of silver carbonate or silver oxide at temperatures between –30° and 100° C., but preferably at temperatures between –10° and 80° C.

e) to prepare 1,3,4-oxathiazole, 1,3,4-thiadiazole and 1,3,4-triazole derivatives of the general formula I:
cyclization of a compound optionally formed in the reaction mixture, of the general formula

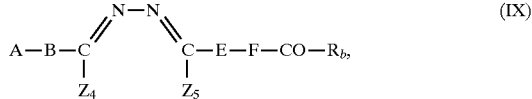

(IX)

in which

Z$_4$ and Z$_5$, which can be identical or different, are halogen atoms, amino groups optionally substituted by R$_7$, R$_7$ being as defined at the outset, hydroxyl, alkoxy, mercapto or alkylmercapto groups, one of the radicals R' or R" is an A—B—C group and the other of the radicals R' or R" is an R$_b$O—CO—E—D group, and, if necessary, subsequent alkylation.

The reaction is expediently carried out in a solvent such as tetrahydrofuran, dioxane, 1,2-dichlorobenzene or pyridine at temperatures up to the boiling point of the solvent used, e.g. at temperatures between 20° and 180° C.

If in a tautomeric compound of the general formula VI Z$_4$ and Z$_5$ are each a hydroxyl group, to prepare a 1,3,4-oxadiazole derivative the reaction is preferably carried out in the presence of a dehydrating agent such as thionyl chloride, to prepare a 1,3,4-thiadiazole derivative the reaction is preferably carried out in the presence of a sulphur-introducing reagent such as, for example, 2,4-bis(4-methoxy-phenyl)-1,3-dithia-2,4-diphosphetane-2,4-disulphide and to prepare a 1,3,4-triazole derivative the reaction is preferably carried out in the presence of a halogen-introducing agent such as phosphorus trichloride and in the presence of aniline.

In the reactions described above, reactive groups which may be present such as carboxyl, amino or imino groups are protected during the reaction by customary protective groups which are removed again after the reaction.

For example, a suitable protective radical for a carboxyl group is the trimethylsilyl, methyl, ethyl, tert-butyl, benzyl or tetrahydropyranyl group and a suitable protective radical for an amino or imino group is the formyl, acetyl, trifluoroacetyl, allyloxycarbonyl, ethoxycarbonyl, tert-butoxycarbonyl, benzyloxycarbonyl, benzyl, methoxybenzyl or 2,4-dimethoxybenzyl group and, for the amino group, additionally the phthalyl group.

A protective radical used is optionally removed subsequently, for example, hydrolytically in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as sodium hydroxide or lithium hydroxide or by means of ether cleavage, e.g. in the presence of iodotrimethylsilane, at temperatures between 0° and 120° C., preferably at temperatures between 10° and 100° C.

However, a benzyl, methoxybenzyl or benzyloxycarbonyl radical is removed, for example, hydrogenolytically, e.g. with hydrogen in the presence of a catalyst such as palladium/carbon in a solvent such as methanol, ethanol, ethyl acetate or glacial acetic acid, if appropriate with addition of an acid such as hydrochloric acid, at temperatures between 0° and 100° C., but preferably at temperatures between 20° and 60° C., and at a hydrogen pressure of 1 to 7 bar, but preferably of 3 to 5 bar. However, the removal of a 2,4-dimethoxybenzyl radical is preferably carried out in trifluoroacetic acid in the presence of anisole.

A tert-butyl or tert-butoxycarbonyl radical is preferably removed by treatment with an acid such as trifluoroacetic acid or hydrochloric acid or by treatment with iodotrimethylsilane, if appropriate using a solvent such as methylene chloride, dioxane, methanol or ether.

A trifluoroacetyl radical is preferably removed by treatment with an acid such as hydrochloric acid, if appropriate in the presence of a solvent such as acetic acid, at temperatures between 50° and 120° C. or by treatment with sodium hydroxide solution or aqueous lithium hydroxide solution, if appropriate in the presence of a solvent such as tetrahydrofuran or methanol, at temperatures between 0° and 50° C.

An allyloxycarbonyl radical is removed by treatment with a catalytic amount of tetrakis(triphenylphosphine)palladium (0), preferably in a solvent such as tetrahydrofuran and preferably in the presence of an allyl group acceptor such as morpholine or 1,3-dimedone at temperatures between 0° and 100° C., preferably at room temperature and under inert gas, or by treatment with a catalytic amount of tris(triphenylphosphine)rhodium(I) chloride in a solvent such as aqueous ethanol and, if appropriate, in the presence of a base such as 1,4-diaza-bicyclo[2.2.2]octane at temperatures between 20° and 70° C.

A phthalyl radical is preferably removed in the presence of hydrazine or a primary amine such as methylamine, ethylamine or n-butylamine in a solvent such as methanol, ethanol, isopropanol, toluene/water or dioxane at temperatures between 20° and 50° C.

Furthermore, the compounds of the general formula I obtained, as has already been mentioned at the outset, can be separated into their enantiomers and/or diastereomers. Thus, for example, cis/trans mixtures can be separated into their cis and trans isomers, and compounds having at least one optically active carbon atom can be separated into their enantiomers.

Thus, for example, the cis/trans mixtures obtained can be separated by chromatography into their cis and trans isomers, the compounds of the general formula I obtained, which occur as racemates, can be separated by methods known per se (see Allinger N. L. and Eliel E. L. in "Topics in Stereochemistry", Vol. 6, Wiley Interscience, 1971) into their optical antipodes and compounds of the general formula I having at least 2 stereogenic centres can be separated on the basis of their physicochemical differences by methods known per se, e.g. by chromatography and/or fractional crystallization, into their diastereomers which, if they are obtained in racemic form, can then be separated as mentioned above into the enantiomers.

Separation of the enantiomers is preferably carried out by column separation on chiral phases or by recrystallization from an optically active solvent or by reaction with an optically active substance forming salts or derivatives such as, for example, esters or amides with the racemic compound, in particular acids and their activated derivatives or alcohols, and separation of the diastereomeric salt mixture or derivative obtained in this way, e.g. on the basis of differing solubilities, it being possible to liberate the free antipodes from the pure diastereomeric salts or derivatives by the action of suitable agents.

Particularly customary, optically active acids are, for example, the D- and L-forms of tartaric acid or dibenzoyltartaric acid, di-o-tolyltartaric acid, malic acid, mandelic acid, camphorsulphonic acid, glutamic acid, aspartic acid or quinic acid. A suitable optically active alcohol is, for example, (+)- or (−)-menthol and a suitable optically active acyl radical in amides is, for example, (+)- or (−)-menthyloxycarbonyl.

In addition, the compounds of the formula I obtained can be converted into their salts, in particular, for pharmaceutical administration, into their physiologically tolerable salts with inorganic or organic acids. Suitable acids for this purpose are, for example, hydrochloric acid, hydrobromic acid, sulphuric acid, phosphoric acid, fumaric acid, succinic acid, lactic acid, citric acid, tartaric acid or maleic acid.

Additionally, the novel compounds of the formula I thus obtained, if these contain a carboxyl group, can if desired then be converted into their salts with inorganic or organic bases, in particular, for pharmaceutical administration, into their physiologically tolerable salts. Suitable bases in this context are, for example, sodium hydroxide, potassium hydroxide, arginine, cyclohexylamine, ethanolamine, diethanolamine and triethanolamine.

The compounds used as starting substances are known from the literature in some cases or are obtained by processes known from the literature (see Examples I to XXXVIII).

As already mentioned at the outset, the novel 5-membered heterocycles of the general formula I and their salts, in particular their physiologically tolerarable salts with inorganic or organic acids or bases, have useful pharmacological properties, in addition to an anti-inflammatory and osteoclastic effect, but in particular antithrombotic, antiaggregatory and antitumour or antimetastatic effects.

For example, the compounds of the general formula I were investigated for their biological effects as follows:
1. Inhibition of the binding of $^3$H-BIBU 52 to human platelets A suspension of human platelets in plasma is incubated with $^3$H-BIBU 52 [=(3S,5S)-5-[(4'-amidino-4-biphenylyl)oxy-methyl]-3-[(carboxyl)methyl]-2-pyrrolidinone[3-$^3$H-4-bi-phenylyl]], which replaces the ligand $^{125}$I-fibrinogen known from the literatre, (see DE-A-4,214,245) and various concentrations of the substance to be tested. The free and bound ligand is separated by centrifugation and quantitatively determined by scintillation counting. From the measurements, the inhibition of $^3$H-BIBU 52 binding by the test substance is determined.

For this purpose, donor blood is taken from an anticubital vein and anticoagulated with trisodium citrate (final concentration 13 mM). The blood is centrifuged at 170×g for 10 minutes and the supernatant platelet-rich plasma (PRP) is removed. The remaining blood is intensely centrifuged off once more to obtain plasma. The PRP is diluted 1:10 with autologous plasma. 750 ml are incubated with 50 ml of physiological saline solution, 100 ml of test substance solution, 50 ml of $^{14}$C-sucrose (3700 Bq) and 50 ml of $^3$H-BIBU-52 (final concentration: 5 nM at room temperature for 20 minutes. To measure the non-specific binding, instead of the test substance 5 ml of BIBU 52 (final concentration: 30 mM) are employed. The samples are centrifuged at 10,000×g for 20 seconds and the supernatant is removed. 100 ml of this are measured to determine the free ligand. The pellet is dissolved in 500 ml of 0.2N NaOH, and 450 ml are treated with 2 ml of scintillator and 25 ml of 5N Hcl and measured. The residual plasma still remaining in the pellet is determined from the $^{14}$C content, the bound ligand from $^3$H-measurement. After removal of the non-specific binding, the pellet activity is plotted against the concentration of the test substance and the concentration determined for a 50% inhibition of binding.

2. Antithrombotic effect

Methodology

Platelets aggregation is measured by the method of Born and Cross (J. Physiol. 170, 397 (1964)) in platelet-rich plasma of healthy subjects. To inhibit clotting, the blood is treated with sodium citrate, 3.14% in the volume ratio 1:10.

Collagen-induced aggregation

The course of the decrease in the optical density of the platelet suspension is measured and recorded photometrically after addition of the aggregation-inducing substance. From the angle of inclination of the density curve, the aggregation rate is deduced. The point of the curve at which the greatest light transmission exists is used to calculate the optical density.

The amount of collagen is selected to be as low as possible, but in such a way that a reaction curve with an irreversible course results. Commercially available collagen from Hormonchemie, Munich, is used.

Before the addition of collagen, the plasma is in each case incubated at 37° C. with the substance for 10 minutes.

From the measurements obtained, an $EC_{50}$ is determined graphically which relates to a 50% change in the optical density in the sense of an inhibition of aggregation.

The following table contains the results found:

| Substance (Example No.) | Fibrinogen binding test $IC_{50}$ [$\mu$M] | Inhibition of platelet aggregation $EC_{50}$ [$\mu$M] |
|---|---|---|
| 2(3) | 0.300 | 0.14 |
| 4 | 0.120 | 0.16 |
| 4(3) | 0.045 | 0.13 |
| 4(6) | 0.064 | 0.17 |
| 4(8) | 2.500 | 1.80 |
| 4(27) | 0.190 | 0.28 |
| 5(2) | 1.600 | 3.80 |
| 4(19) | 0.038 | 0.10 |
| 4(20) | 0.063 | 0.12 |
| 2(12) | 0.072 | 0.14 |

On account of their inhibitory effect on cell-cell or cell-matrix interactions, the novel 5-membered heterocycles of the general formula I and their physiologically tolerable salts are suitable for the control or prevention of illnesses in which relatively small or relatively large cell aggregates occur or cell-matrix interactions play a part, e.g. in the control or prevention of venous and arterial thromboses, of cerebrovascular disorders, of pulmonary embolisms, of cardiac infarct, of arteriosclerosis, of osteoporosis and of metastasis of tumours and disorders of the interactions of cells with one another or with solid structures genetically related to the therapy or alternatively acquired. Furthermore, these compounds are suitable for concomitant therapy in thrombolysis with fibrinolytics or vascular interventions such as transluminal angioplasty or alternatively in the therapy of states of shock, psoriasis, diabetes and of inflammations.

For the control or prevention of the above-mentioned illnesses, the dose is between 0.1 mg and 30 mg/kg of body weight, preferably 1 mg to 15 mg/kg of body weight, with up to 4 doses per day. For this purpose, the compounds of the formula I prepared according to the invention can be incorporated, if appropriate in combination with other active substances such as thromboxane receptor antagonists and thromboxane synthesis inhibitors or combinations thereof, serotonin antagonists, -receptor antagonists, alkyl nitrates such as glyceryl trinitrate, phosphodiesterase inhibitors, prostacyclin and its analogues, fibrinolytics such as tPA, prourokinase, urokinase, streptokinase, or anticoagulants such as heparin, dermatan sulphate, activated protein C, vitamin K antagonists, hirudine, inhibitors of thrombin or other activated clotting factors, together with one or more inert customary excipients and/or diluents, e.g. with maize starch, lactose, cane sugar, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fat-containing substances such as hard fat or suitable mixtures thereof, in customary pharmaceutical preparations such as tablets, coated tablets, capsules, powders, suspensions, solutions, sprays or suppositories.

The following examples are intended to illustrate the invention in greater detail:
Preparation of the starting compounds

EXAMPLE I 1-(tert-Butoxycarbonyl)-4-piperidylcarbohydrazide

A solution of 19.1 g of 1-(tert-butoxycarbonyl)-4-piperidyl-carboxylic acid, 32.1 g of 2-[(1H)-benzotriazol-1-yl]-1,1,3,3-tetramethyluronium tetrafluoroborate, 30.4 g of triethylamine and 90 g of hydrazine hydrate is stirred at room temperature for 5 hours in 300 ml of dimethylformamide. The solvent is evaporated under reduced pressure and the residue is chromatographed on silica gel using methylene chloride/methanol/conc. ammonia (9:1:0.1).

Yield: 11.0 g (55% of theory), melting point: 106°–108° C.

$R_f$: 0.47 (silica gel; methylene chloride/methanol/conc. ammonia=9:1:0.1)

EXAMPLE II

N-[1-(tert-Butoxycarbonyl)-4-piperidylcarbonyl]-N'-[(methoxycarbonyl)carbonyl]hydrazine A solution of 1.22 g of freshly distilled methyl oxalyl chloride in 15 ml of tetrahydrofuran is added dropwise at 0° C. to a solution of 2.43 g of 1-(tert-butoxycarbonyl)-4-piperidylcarbohydrazide in 25 ml of tetrahydrofuran. The mixture is stirred at room temperature for 16 hours and the precipitate is filtered off on a suction filter. The filtrate is evaporated under reduced pressure and the crude product is reacted without further purification.

Yield: 3.5 g (quantitative)

EXAMPLE III

2-[1-(tert-Butoxycarbonyl)-4-piperidyl]-5-methoxycarbonyl-1,3,4-thiadiazole

A suspension of 3.27 g of N-[1-(tert-butoxycarbonyl)-4-piperidylcarbonyl]-N'-[(methoxycarbonyl)carbonyl] hydrazine and 4.05 g of 2,4-bis(4-methoxyphenyl)-1,3-dithia-2,4-di-phosphetane-2,4-disulphide in 30 ml of tetrahydrofuran is heated at reflux for 30 minutes. The solvent is evaporated under reduced pressure and the residue is chromatographed on silica gel using ethyl acetate/cyclohexane (4:1).

Yield: 2.5 g (76% of theory), melting point: 107°–110° C.

$R_f$: 0.60 (silica gel; ethyl acetate/cyclohexane=4:1)

EXAMPLE IV

2-[1-(tert-Butoxycarbonyl)-4-piperidyl]-5-carboxy-1,3,4-thiadiazole

A solution of 5.2 g 2-[1-(tert-butoxycarbonyl)-4-piperidyl]-5-methoxycarbonyl-1,3,4-thiadiazole in 24 ml of 1M of sodium hydroxide solution and 100 ml of methanol is stirred at room temperature for 10 minutes. It is neutralized by dropwise addition of 0.1M hydrochloric acid and the methanol is largely evaporated under reduced pressure on a rotary evaporator at a bath temperature of 35° C. The precipitate is filtered off on a suction filter, washed with a little water and dried.

Yield: 3.0 g (60% of theory), melting point: 298°–302° C. (dec.)

$R_f$: 0.24 (silica gel; methylene chloride/methanol/conc. ammonia=4:1:0.2)

EXAMPLE V 1-(Phenylmethoxycarbonyl)-4-piperidylcarboxamide 39.9 g of benzyl chloroformate and 234 ml of 1M sodium hydroxide solution are successively added dropwise to a solution of 30.0 g of 4-piperidylcarboxamide in methylene chloride such that a pH of 9 is maintained. The mixture is stirred at room temperature for 1 hour. The organic phase is washed with water and saturated sodium chloride solution and dried over sodium sulphate, and the solvent is evaporated under reduced pressure.

Yield: 61.4 g (quantitative), $R_f$: 0.49 (silica gel; methylene chloride/methanol/conc. ammonia=9:1:0.1)

The following compound is obtained analogously to Example V:

(1) 4-(2-Carboxyethyl)-1-benzyloxycarbonylpiperidine 4-(2-Carboxyethyl)piperidine hydrochloride (melting point: 240°–250° C., prepared by hydrogenation of 3-(4-pyridyl) acrylic acid in glacial acetic acid in the presence of platinum oxide and subsequent treatment with hydrochloric acid) is employed. After stirring for 2 hours, the reaction solution is brought to pH 5 by addition of 1N hydrochloric acid. The aqueous phase is extracted several times with methylene chloride. The combined organic phases are dried and the solvent is evaporated under reduced pressure. The crude product is chromatographed on silica gel using methylene chloride/methanol/conc. ammonia (4:1:0.2).

$R_f$: 0.29 (silica gel; methylene chloride/methanol/conc. ammonia=4:1:0.25)

EXAMPLE VI 1-(Phenylmethoxycarbonyl)-4-piperidylthiocarboxamide

A solution of 20.0 g of 1-(phenylmethoxycarbonyl)-4-piperidylcarboxamide and 15.4 g of 2,4-bis(4-methoxyphenyl)-1,3-dithia-2,4-diphosphetane-2,4-disulphide in 500 ml of tetrahydrofuran is heated at reflux for 6 hours. The solvent is evaporated under reduced pressure and the residue is partitioned between saturated sodium hydrogencarbonate solution and ethyl acetate. The organic phase is dried, the solvent is evaporated and the residue is chromatographed on silica gel using ethyl acetate/cyclohexane (1:1).

Yield: 8.47 g (41% of theory),
mass spectrum: $M^+=278$
$R_f$: 0.26 (silica gel; ethyl acetate/cyclohexane=1:2)

The following compound is obtained analogously to Example VI:
(1) 4-(2-Aminothiocarbonylethyl)-1-phenylmethoxycarbonylpiperidine The mixture is heated at reflux for 2 hours. After extraction by shaking, the residue is triturated with ether and filtered off on a suction filter.

Melting point: 148°–154° C.
Mass spectrum: $(M+H)^+=307$
$R_f$: 0.52 (silica gel; methylene chloride/methanol/conc. ammonia=9:1:0.1)

EXAMPLE VII

2-[1-(Phenylmethoxycarbonyl)-4-piperidyl]-4-ethoxycarbonyl-1,3-thiazole

A solution of 4.0 g of 1-(phenylmethoxycarbonyl)-4-piperidylthiocarboxamide and 3.36 g of ethyl bromopyruvate in 50 ml of ethanol is stirred at room temperature for 6 hours. The solvent is evaporated and the residue is chromatographed on silica gel using ethyl acetate/cyclohexane (1:2).

Yield: 3.1 g (59% of theory),
mass spectrum: $M^+=374$
$R_f$: 0.26 (silica gel; ethyl acetate/cyclohexane=1:2)

EXAMPLE VIII

2-[1-(Phenylmethoxycarbonyl)-4-piperidyl]-4-carboxy-1,3-thiazole

Sufficient methanol is added to a suspension of 2.43 g of 2-[1-(phenylmethoxycarbonyl)-4-piperidyl]-4-ethoxycarbonyl-1,3-thiazole in 33 ml of 1M sodium hydroxide solution and 50 ml of tetrahydrofuran such that a clear solution results. The mixture is stirred at room temperature for 10 minutes and neutralized with 1M hydrochloric acid. The organic solvents are evaporated under reduced pressure and the aqueous phase is extracted with ethyl acetate. The organic phase is dried and the solvent is evaporated under reduced pressure.

Yield: 2.25 g (quantitative) of yellowish oil,
mass spectrum: $M^+=346$
$R_f$: 0.20 (silica gel; methylene chloride/methanol/conc. ammonia=4:1:0.25)

The following compounds are obtained analogously to Example VIII:
(1) 5-Carboxy-4-methyl-2-[1-(phenylmethoxycarbonyl)-4-piperidyl]-1,3-thiazole Instead of 1M sodium hydroxide solution 1M lithium hydroxide solution is employed.

Melting point: 126°–128° C.
$R_f$: 0.14 (silica gel; methylene chloride/methanol=15:1)

(2) 1-[1-(tert-Butoxycarbonyl)-4-piperidyl]-4-carboxyimidazole

Melting point: 206°–208° C. (dec.)
$R_f$: 0.09 (silica gel; methylene chloride/methanol/conc. ammonia=4:1:0.25)

(3) trans-3-[1-[1-(tert-Butoxycarbonyl)-4-piperidyl]-4-imidazolyl]acrylic acid

The mixture is stirred at room temperature for 2 hours. After neutralization with 1M hydrochloric acid, the organic solvent is evaporated under reduced pressure and the aqueous phase is cooled in an ice bath. The precipitate is filtered off on a suction filter.

Melting point: 305°–306° C. (dec.)
$R_f$: 0.39 (silica gel; methylene chloride/methanol/conc. ammonia=4:1:0.25)

(4) 1-[2-[1-(tert-Butoxycarbonyl)-4-piperidyl]ethyl]-4-carboxyimidazole

The mixture is stirred at room temperature for 16 hours. After neutralization with 1M hydrochloric acid, the product crystallizes out.

Melting point: 243° C. (dec.)
$R_f$: 0.51 (silica gel; methylene chloride/methanol/conc. ammonia=4:1:0.25)

(5) 2-[2-(1-Benzyloxycarbonyl-4-piperidyl)ethyl]-5-carboxy-4-methyl-1,3-thiazole The hydrolysis is carried out using lithium hydroxide in tetrahydrofuran/water (4:5). The crude product is chromatographed on silica gel using methylene chloride/methanol/conc. ammonia (4:1:0.2).

Melting point: 132°–136° C.
Mass spectrum: $M^+=388$
$R_f$: 0.38 (silica gel; methylene chloride/methanol/conc. ammonia=4:1:0.2)

(6) 5-Carboxy-2-[1-(phenylmethoxycarbonyl)-4-piperidyl]-1,3-thiazole

Instead of 1M sodium hydroxide solution 1M lithium hydroxide solution is employed.

$R_f$: 0.16 (silica gel; methylene chloride/methanol=10:1)

EXAMPLE IX

2-[1-(Phenylmethoxycarbonyl)-4-piperidyl]-4-methyl-5-ethoxycarbonyl-1,3-thiazole A solution of 4.0 g of 1-(phenylmethoxycarbonyl)-4-piperidylthiocarboxamide and 2.2 ml of ethyl 2-chloroacetate in 15 ml of absolute ethanol is heated at reflux for 2 hours. The solvent is evaporated under reduced pressure and the residue is chromatographed on silica gel using ethyl acetate/cyclohexane (1:2 to 1:1).

Yield: 3.35 g (60% of theory),
mass spectrum: $M^+=388$
$R_f$: 0.46 (silica gel; ethyl acetate/cyclohexane=1:2)

The following compounds are obtained analogously to Example IX:
(1) 5-Ethoxycarbonyl-4-methyl-2-[2-(1-phenylmethoxycarbonyl-4-piperidyl)ethyl3-1,3-thiazole 4-(2-Aminothiocarbonylethyl)-1-phenylmethoxycarbonylpiperidine is employed. The reaction solution is heated at reflux for 6 hours. After 2 and 4 hours, 0.2 equivalents of ethyl 2-chloroacetate are added in each case. The residue is dissolved in ethyl acetate and extracted with saturated sodium hydrogencarbonate solution and saturated sodium chloride solution. The organic phase is dried and evaporated. The residue is chromatographed on silica gel using cyclohexane/ethyl acetate (2:1).

Mass spectrum: M$^+$=416

R$_f$: 0.39 (silica gel; cyclohexane/ethyl acetate=2:1)

(2) 2-[1-(Phenylmethoxycarbonyl)-4-piperidyl]-5-ethoxycarbonyl-1,3-thiazole

Ethyl 2-chloro-3-hydroxyacrylate is employed. The reaction solution is heated at reflux for 2.5 days. After 2 days, a further 0.5 equivalents of ethyl 2-chloro-3-hydroxyacrylate are added. The reaction solution is evaporated and the residue is chromatographed on silica gel using cyclohexane/ethyl acetate (2:1).

R$_f$: 0.26 (silica gel; cyclohexane/ethyl acetate=2:1)

(3) 5-Ethoxycarbonyl-2-[2-(1-phenylmethoxycarbonyl-4-piperidyl)ethyl]-1,3-thiazole 4-(2-Aminothiocarbonylethyl)-1-phenylmethoxycarbonylpiperidine and 2-chloro-3-hydroxyacrylate are employed. The reaction solution is heated at reflux for 7 hours. The residue is chromatographed on silica gel using cyclohexane/ ethyl acetate (2:1).

Mass spectrum: M$^+$=402

R$_f$: 0.23 (silica gel; cyclohexane/ethyl acetate=2:1)

EXAMPLE X

1-[1-(tert-Butoxycarbonyl)-4-piperidyl]-4-methoxycarbonyl-imidazole 1.5 g of sodium hydride (60% strength dispersion in mineral oil) are added to a solution of 4.3 g of methyl 4(5)-imid-azolecarboxylate in 100 ml of dimethylformamide and the mixture is stirred at room temperature for 1 hour. 9.5 g of 1-(tert-butoxycarbonyl)-4-piperidyl methanesulphonate are added and the mixture is stirred at 60° C. for 5 days. The solvent is evaporated under reduced pressure and the residue is taken up in ethyl acetate. The organic phase is washed with water and dried, the solvent is evaporated and the residue is chromatographed on silica gel using methylene chloride/methanol/conc. ammonia (39:1:0.1 to 19:1:0.1).

Yield: 2.54 g (24% of theory), mass spectrum: M$^+$=309

R$_f$: 0.52 (silica gel; methylene chloride/methanol/conc. ammonia=9:1:0.1)

The following compounds are obtained analogously to Example X:

(1) Methyl trans-3-[1-[1-(tert-butoxycarbonyl)-4-piperidyl]-4-imidazolyl]acrylate Methyl 3-[4(5)-imidazolyl]acrylate is employed.

R$_f$: 0.55 (silica gel; methylene chloride/methanol/conc. ammonia=9:1:0.1)

(2) 1-[2-[1-(tert-Butoxycarbonyl)-4-piperidyl]ethyl]-4-methoxycarbonylimidazole

[2-[1-(tert-Butoxycarbonyl)-4-piperidyl]ethyl] methanesulphonate (prepared by reduction of methyl [1-(tertbutoxycarbonyl)-4-piperidyl]acetate with lithium borohydride in tetrahydrofuran and subsequent esterification with methanesulphonyl chloride in methylene chloride in the presence of triethylamine; melting point: 85.5°–87.5° C.) is employed. The mixture is stirred at room temperature for 4 days.

R$_f$: 0.51 (silica gel; methylene chloride/methanol/conc. ammonia=9:1:0.1)

(3) 1-[1-(tert-Butoxycarbonyl)-4-piperidyl]-4-nitroimidazole

4(5)-Nitroimidazole is employed. The reaction solution is stirred at 55° C. for 14 days. After addition of 2.0 g of potassium carbonate, the mixture is stirred at 70° C. for 4 days.

Melting point: 153°–154° C.

R$_f$: 0.55 (silica gel; methylene chloride/methanol/conc. ammonia=9:1:0.1)

EXAMPLE XI

Methyl trans-3-(4-imidazolyl)acrylate

A solution of 6.0 g of trans-3-(4-imidazolyl)acrylic acid in 100 ml of methanol and 20 ml of ethereal hydrochloric acid is heated under reflux for 8 hours. The solvent is evaporated under reduced pressure and the residue is triturated with acetone, filtered off with suction and dried.

Yield : 8.1 g (99% of theory),

R$_f$: 0.91 (silica gel; methylene chloride/methanol/conc. ammonia=9:1:0.25)

EXAMPLE XII tert-Butyl [4-(aminocarbonyl)piperidin-1-yl]acetate 9.0 g of piperidine-4-carboxamide, 11.3 g of tert-butyl bromoacetate and 10.4 g of potassium carbonate in 100 ml of acetone are stirred at room temperature for 4 hours. The solvent is evaporated under reduced pressure and the residue is dissolved in water. The aqueous phase is extracted with ethyl acetate, the organic phase is dried and the solvent is evaporated under reduced pressure. The crude product is chromatographed on silica gel using methylene chloride/methanol/conc. ammonia (9:1:0.1).

Yield : 15.0 g (88% of theory),

R$_f$: 0.47 (silica gel; methylene chloride/methanol/conc. ammonia=9:1:0.1)

EXAMPLE XIII tert-Butyl [4-(Aminomethyl)piperidin-1-yl]acetate

A solution of 2.42 g of tert-butyl [4-(aminocarbonyl)piperidin-1-yl]acetate in 30 ml of tetrahydrofuran is added dropwise to 20 ml of a 1M solution of diborane in tetrahydrofuran and the mixture is heated at reflux for 4 hours. 10 ml of a 1M solution of diborane in tetrahydrofuran are added and the mixture is heated at reflux for a further 5 hours. Water is added and the mixture is extracted with ethyl acetate. The aqueous phase is evaporated under reduced pressure and the residue is chromatographed on silica gel using methylene chloride/methanol/conc. ammonia (4:1:0.25).

Yield: 0.95 g (42% of theory),

R$_f$: 0.11 (silica gel; methylene chloride/methanol/conc. ammonia=9:1:0.1)

EXAMPLE XIV

Ethyl 1-(2-Dibenzylaminoethyl)-4-piperidinecarboxylate

A solution of 9.07 g of N-(2-chloroethyl)dibenzylamine hydrochloride, 4.6 ml of ethyl 4-piperidinecarboxylate and 10.3 ml of ethyldiisopropylamine in 20 ml of methanol is heated at reflux for 5 hours. The solvent is evaporated under reduced pressure and the residue is chromatographed on silica gel using methylene chloride/methanol/conc. ammonia (30:1:0.25).

Yield: 7.90 g (69% of theory), $R_f$: 0.64 (silica gel; methylene chloride/methanol/conc. ammonia=9:1:0.1)

EXAMPLE XV

Ethyl 1-(2-aminoethyl)-4-piperidinecarboxylate hydrochloride

A solution of 7.9 g of ethyl 1-(2-dibenzylaminoethyl)-4-piperidinecarboxylate in 21 ml 1N hydrochloric acid and 100 ml of ethanol is hydrogenated with hydrogen in the presence of 1.0 g of 10% strength palladium on carbon at a hydrogen pressure of 3 bar and at a temperature of 50° C. The catalyst is filtered off and the solvent is evaporated under reduced pressure. The residue is triturated with acetone, filtered off on a suction filter and dried.

Yield: 3.5 g (71% of theory),

Melting point: 128°–130° C.

$R_f$: 0.12 (silica gel; methylene chloride/methanol/conc. ammonia=9:1:0.1)

EXAMPLE XVI 1-(tert-Butoxycarbonyl)-4-hydroxypiperidine

A solution of 31.7 g of di-tert-butyl pyrocarbonate in 100 ml of tetrahydrofuran and then 100 ml of 1N sodium hydroxide solution are added to 15.0 g of 4-hydroxypiperidine. The mixture is stirred at room temperature for 16 hours. The suspension is extracted with ethyl acetate. The organic phase is washed with saturated sodium chloride solution and dried over sodium sulphate. The solvent is evaporated under reduced pressure.

Yield: 28.5 g (98% of theory), $R_f$: 0.23 (silica gel; methylene chloride/methanol=15:1)

EXAMPLE XVII 1-(tert-Butoxycarbonyl)-4-[(2-cyanoethyl)oxy]piperidine 30 mg of potassium tert-butoxide are added to a solution of 6.04 g of 1-(tert-butoxycarbonyl)-4-hydroxypiperidine in 6.6 ml of acrylonitrile and 10 ml of dioxane and the mixture is heated at reflux for 4 hours under a nitrogen atmosphere. A further 3 ml of acrylonitrile and 30 mg of potassium tert-butoxide are added and the mixture is heated for a further 2 hours. The reaction solution is evaporated and the residue is partitioned between water and ethyl acetate. The organic phase is dried and evaporated. The crude product is chromatographed on silica gel using cyclohexane/ethyl acetate (2:1).

Yield: 4.49 g (59% of theory) of an oil.

$R_f$: 0.60 (silica gel; cyclohexane/ethyl acetate=1:1)

EXAMPLE XVIII

4-[(2-Methoxycarbonylethyl)oxy]piperidine hydrochloride

With exclusion of water, a solution of 4.47 g of 1-(tert-butoxycarbonyl)-4-[(2-cyanoethyl)oxy]piperidine in 20 ml of absolute methanol and 20 ml of ethereal hydrochloric acid is heated under reflux for several hours. The solvent is evaporated under reduced pressure and the residue is partitioned between 20 ml of saturated potassium carbonate solution and ether. The organic phase is dried and evaporated. 5 ml of water and 5 ml of conc. hydrochloric acid are added to the residue and the mixture is stirred at room temperature for 16 hours. The solvent is evaporated. 20 ml of absolute methanol and 20 ml of ethereal hydrochloric acid are added and the mixture is stirred at room temperature for 16 hours. The solvent is evaporated and the crude product is chromatographed on silica gel using methylene chloride/methanol/conc. ammonia (9:1:0.1).

Yield: 1.7 g (43% of theory), $R_f$: 0.24 (silica gel; methylene chloride/methanol/conc. ammonia=9:1:0.1)

EXAMPLE XIX 4-(2-Aminocarbonylethyl)-1-benzyloxycarbonylpiperidine

A suspension of 18.5 g of 4-(2-carboxyethyl)-1-benzyloxycarbonylpiperidine, 10.1 g of triethylamine and 25.7 g of 2-[(1H)-benzotriazol-1-yl]-1,1,3,3-tetramethyluronium tetrafluoroborate in 300 ml of tetrahydrofuran is stirred at room temperature for 2 hours. The suspension is added dropwise with good stirring to 250 ml of concentrated ammonia. The mixture is stirred at room temperature for 3 days, the organic phase is separated off and the aqueous phase is extracted twice with ethyl acetate. The combined organic phases are washed with saturated sodium chloride solution and dried over sodium sulphate, and the solvent is evaporated under reduced pressure. The solid is triturated with ethyl acetate and filtered off on a suction filter.

Yield: 12.0 g (65% of theory),

Melting point: 104°–107° C.

$R_f$: 0.72 (silica gel; methylene chloride/methanol/conc. ammonia=4:1:0.2)

EXAMPLE XX

4-Amino-1-[1-(tert-butoxycarbonyl)-4-piperidyl]imidazole

A solution of 480 mg of 1-[1-(tert-butoxycarbonyl)-4-piperidyl]-4-nitroimidazole in 20 ml of ethanol is hydrogenated at room temperature with hydrogen in the presence of 0.2 g of 10% strength palladium on carbon at a hydrogen pressure of 3 bar. The catalyst is filtered off and the solvent is evaporated under reduced pressure. The residue is dissolved in tetrahydrofuran and the solution is evaporated. The product is employed without further purification.

Yield: 450 mg (quantitative), $R_f$: 0.36 (silica gel; methylene chloride/methanol/conc. ammonia=9:1:0.1)

EXAMPLE XXI

Methyl trans-4-(N-methanesulphonylamino)cyclohexanecarboxylate

A solution of 5.2 g of methyl trans-4-aminocyclohexanecarboxylate hydrochloride, 2.32 ml of methanesulphonyl chloride in 100 ml of methylene chloride and 35 ml of pyridine is stirred at room temperature for 2 days. The reaction solution is evaporated under reduced pressure and the residue is dissolved in ethyl acetate. The organic phase is washed with water, 1M hydrochloric acid, saturated sodium hydrogencarbonate solution and saturated sodium chloride solution, dried and evaporated. The crude product is triturated with ether and filtered off with suction.

Yield: 3.8 g (60% of theory), $R_f$: 0.62 (silica gel; methylene chloride/methanol=15:1)

EXAMPLE XXII

Methyl trans-4-(N-tert-Butoxycarbonylmethyl-N-methanesulphonylamino)cyclohexanecarboxylate A suspension of 3.8 g of methyl trans-4-(N-methanesulphonyl-amino)cyclohexanecarboxylate, 4.7 ml of tert-butyl bromoacetate and 6.0 g of potassium carbonate in 50 ml of acetone is heated at reflux for 10 hours. The reaction solution is evaporated and the residue is partitioned between water and ethyl acetate. The organic phase is washed with saturated sodium chloride solution, dried and concentrated in a rotary evaporator. The crude product is triturated with ether and filtered on a suction filter.

Yield: 4.6 g (82% of theory), melting point: 116°–118° C.

$R_f$: 0.69 (silica gel; methylene chloride/methanol/conc. ammonia=9:1:0.1)

EXAMPLE XXIII trans-4-(N-tert-Butoxycarbonylmethyl-N-methanesulphonylamino)cyclohexanecarboxylic acid Prepared analogously to Example VIII. The mixture is stirred at room temperature for 4 hours. After neutralization, the organic solvent is evaporated and the solution is cooled. The precipitate is filtered off on a suction filter and dried.

Yield: 2.58 g (88% of theory),

Melting point: 143°–144° C.

$R_f$: 0.35 (silica gel; methylene chloride/methanol=15:1)

EXAMPLE XXIV

Methyl a-(4-benzyloxycarbonylphenoxy)acetate 5.53 g of potassium carbonate are added to a solution of 8.0 g of benzyl 4-hydroxybenzoate in 50 ml of dimethylformamide and the mixture is stirred at room temperature for 30 minutes. 3.3 ml of methyl bromoacetate are added and the mixture is stirred at room temperature for 16 hours. The reaction solution is evaporated and the residue is partitioned between water and ethyl acetate. The organic phase is washed with saturated sodium chloride solution, dried and concentrated in a rotary evaporator.

Yield: 10.5 g (quantitative),

Melting point: 60°–62° C.

$R_f$: 0.55 (silica gel; cyclohexane/ethyl acetate=2:1)

EXAMPLE XXV

Methyl α-(4-Carboxy-phenoxy)acetate

A solution of 10.5 g methyl α-(4-benzyloxycarbonylphenoxy)acetate in 100 ml of methanol is hydrogenated at room temperature with hydrogen in the presence of 2 g of 10% strength palladium on carbon at a hydrogen pressure of 3 bar. The catalyst is filtered off and washed with methylene chloride, and the solvent is evaporated under reduced pressure.

Yield: 6.9 g (94% of theory),

Melting point: 172°–176° C.

$R_f$: 0.36 (silica gel; methylene chloride/methanol=15:1)

EXAMPLE XXVI

5-Carboxy-2-[2-(4-piperidyl)ethyl]-1,3-thiazole hydrochloride

Sufficient methanol such that a solution results is added to a suspension of 1.5 g of 5-ethoxycarbonyl-2-(2-(1-phenylmethoxycarbonyl-4-piperidyl)ethyl]-1,3-thiazole in 40 ml of 6N hydrochloric acid. The mixture is stirred at room temperature for 24 hours and at 60° C. for a further 4 hours. The solvent is evaporated under reduced pressure and the residue (Z-deprotected amine) is dissolved in 50 ml of 6N hydrochloric acid and heated at reflux for 6 hours. The solvent is evaporated.

Yield: 0.84 g (94% of theory), $R_f$: 0.09 (silica gel; methylene chloride/methanol/conc. ammonia=2:1:0.2)

EXAMPLE XXVII

2-[2-(1-tert-Butoxycarbonyl-4-piperidyl)ethyl]-5-carboxy-1,3-thiazole

A solution of 0.74 g of di-tert-butyl pyrocarbonate in 15 ml of tetrahydrofuran is added to a solution of 0.82 g of 5-carboxy-2-[2-(4-piperidyl)ethyl]-1,3-thiazole hydrochloride in 7 ml of 1N hydrochloric acid. The cooling bath is removed and the reaction solution is stirred at room temperature for 24 hours. It is acidified with 1N hydrochloric acid and the aqueous phase is extracted with ethyl acetate. The combined organic phases are dried and the solvent is evaporated. The product crystallizes out from the oil obtained (0.9 g). It is filtered off on a suction filter and washed with a little ether.

Yield: 0.28 g (27% of theory),

Mass spectrum: $M^+=340$ $R_f$: 0.22 (silica gel; methylene chloride/methanol/conc. ammonia=4:1:0.2)

EXAMPLE XXVIII

Ethyl α-(4-Nitrophenoxy)acetate 125.4 g of 4-nitrophenol are dissolved in 1000 ml of absolute dimethylformamide and, after addition of 150.6 g of dried potassium carbonate, the mixture is stirred at room temperature for 45 minutes. 150.6 g of ethyl bromoacetate are added dropwise with stirring and the mixture is warmed at 80° C. for 5 hours. The heating is switched off and the suspension is stirred for 15 hours. The undissolved inorganic salts are filtered off on a suction filter and the filtrate is evaporated under reduced pressure. The residue is partitioned between ethyl acetate and water. The organic phase is extracted twice with water, dried over sodium sulphate, filtered and evaporated. The residue is triturated with petroleum ether and filtered off with suction.

Yield: 192.0 g (95% of theory), $R_f$: 0.7 (silica gel; methylene chloride)

EXAMPLE XXIX

α-1,4-Nitrophenoxy)acetic acid 192.0 g of ethyl α-(4-nitrophenoxy)acetate are added to a solution of 68.2 g of sodium hydroxide in 2 l of water. After about 4 hours everything has dissolved. The solution is brought to pH 3 with good stirring and cooling. The precipitated product is filtered off with suction, washed with water and dried.

Yield: 149.6 g (89% of theory), $R_f$: 0.1 (silica gel; methylene chloride)

EXAMPLE XXX

Cyclohexyl α-(4-nitrophenoxy)acetate 36.2 g of thionyl chloride are added dropwise at −10° C. to −20° C. with good stirring to 200 ml of cyclohexanol in 500 ml of absolute methylene chloride. After addition is complete, the mixture is stirred at low temperature for 30 minutes. 50.0 g of α-(4-nitrophenoxy)acetic acid are added in portions. The suspension is stirred at −10° C. to −20° C. for 2 hours. It is then slowly allowed to warm to room temperature and stirred for a further 16 hours. The clear solution is evaporated under reduced pressure and the oily residue crystallized using petroleum ether.

Yield: 66.7 g (94% of theory), $R_f$: 0.6 (silica gel; methylene chloride)

EXAMPLE XXXI

Cyclohexyl α-(4-aminophenoxy)acetate

A solution of 66.7 g of cyclohexyl α-(4-nitrophenoxy) acetate in 600 ml of ethyl acetate is hydrogenated with hydrogen in the presence of 7.0 g of 10% palladium on carbon at room temperature and a hydrogen pressure of 5 bar. After about 2 hours, hydrogen absorption is complete. The catalyst is filtered off on a suction filter and the filtrate is evaporated. The oil obtained is reacted without further purification.

Yield: 59.0 g (99% of theory), $R_f$: 0.1 (silica gel; methylene chloride)

EXAMPLE XXXII

4-Dibenzylamino-1-(2-methoxycarbonylethyl) piperidine

A solution of 2.9 g of 1-(1-methoxycarbonylethyl)piperid-4-one (prepared by reaction of piperidin-4-one with methyl acrylate in methanol in the presence of potassium carbonate; oil), 3.15 g of dibenzylamine and 4.66 g of sodium triacetoxyborohydride in 60 ml of tetrahydrofuran and 0.96 ml of acetic acid is stirred at 0° C. for 6 hours and then at room temperature for 16 hours. The reaction solution is diluted with ethyl acetate and the organic phase is washed with 1M sodium hydroxide solution and saturated sodium chloride solution. The organic phase is dried over sodium sulphate and evaporated.

Yield: 5.2 g (91% of theory), $R_f$: 0.33 (silica gel; methylene chloride/methanol/conc. ammonia=20:1:0.1)

Example XXXIII

4-Amino-1-(2-methoxycarbonylethyl)piperidine 5.0 g of 4-dibenzylamino-1-(2-methoxycarbonylethyl) piperidine and 4.3 g of ammonium formate in 150 ml of methanol are heated under reflux for 2 hours in the presence of 0.4 g of 10% strength palladium on carbon. The catalyst is filtered off and the filtrate is evaporated under reduced pressure. The residue is chromatographed on silica gel using methylene chloride/methanol/conc. ammonia (9:1:0.1).

Yield: 1.4 g (56% of theory) of an oil, $R_f$: 0.20 (silica gel; methylene chloride/methanol/conc. ammonia=9:1:0.1)

EXAMPLE XXXIV

Benzyl [4-(ethoxycarbonylmethoxy)phenoxy]acetate

A suspension of 9.0 g of benzyl (4-hydroxyphenoxy) acetate [prepared by esterification of (4-hydroxyphenoxy) acetic acid with benzyl alcohol analogously to Example 8; melting point: 69°–71° C.] and 9.7 g of potassium carbonate in 100 ml of dimethylformamide is stirred at room temperature for 30 minutes. 6.7 g of ethyl bromoacetate are added dropwise and the mixture is stirred at room temperature for 16 hours and at 70° C. for 1 hour. The reaction solution is evaporated and the residue is partitioned between ethyl acetate and water. The organic phase is washed with saturated sodium chloride solution, dried and evaporated.

Yield: 11.5 g (96% of theory), melting point: 66°–68° C.

$R_f$: 0.52 (silica gel; cyclohexane/ethyl acetate 2:1)

The following compound is obtained analogously to Example XXXIV:

(1) Benzyl 3-[4-(ethoxycarbonylmethoxy)phenyl] propionate Benzyl 3-(4-hydroxyphenyl)propionate [prepared by esterification of 3-(4-hydroxyphenyl)propionic acid with benzyl alcohol analogously to Example 8; oil, $R_f$: 0.28 (silica gel; cyclohexane/ethyl acetate=2:1)] is employed. The crude product is chromatographed on silica gel using cyclohexane/ethyl acetate (2:1).

$R_f$: 0.58 (silica gel; cyclohexane/ethyl acetate=2:1)

EXAMPLE XXXV

[4-(Ethoxycarbonylmethoxy)phenoxy]acetic acid

Preparation of benzyl [4-(ethoxycarbonylmethoxy) phenoxy]acetate by catalytic hydrogenation analogously to Example 7 in ethyl acetate as solvent.

Melting point: 90°–92° C.

$R_f$: 0.05 (silica gel; cyclohexane/ethyl acetate 2:1)

EXAMPLE XXXVI

1-[[[4-(Ethoxycarbonylmethoxy)phenyl]oxymethyl] carbonyl]-2-[(1-benzyloxycarbonyl-4-piperidyl) carbonyl]hydrazine Preparation of [4-(ethoxycarbonylmethoxy)phenoxy] acetic acid and (1-benzyloxycarbonyl-4-piperidyl) carbohydrazide (prepared analogously to Example I; melting point: 134°–136° C.) analogously to Example 1.

Melting point: 169° C.

$R_f$: 0.45 (silica gel; methylene chloride/methanol/conc. ammonia=9:1:0.1)

EXAMPLE XXXVII

3-[4-(Ethoxycarbonylmethoxy)phenyl]propionic acid

Preparation of benzyl 3-[4-(ethoxycarbonylmethoxy) phenyl]propionate by catalytic hydrogenation analogously to Example 7 in ethyl acetate as solvent.

Melting point: 75°–80° C.

$R_f$: 0.09 (silica gel; methylene chloride/methanol/conc. ammonia=9:1:0.1)

EXAMPLE XXXVIII

1-[[2-[4-(Ethoxycarbonylmethoxy)phenyl]ethyl]carbonyl]-2-[(1-benzyloxycarbonyl-4-piperidyl)carbonyl]hydrazine Preparation of 3-[4-(ethoxycarbonylmethoxy)phenyl]propionic acid and (1-benzyloxycarbonyl-4-piperidyl)carbohydrazide analogously to Example 1.

$R_f$: 0.43 (silica gel; methylene chloride/methanol/conc. ammonia=9:1:0.1)

Preparation of the final products:

EXAMPLE 1

5-[[trans-4-(2-Methoxycarbonylethyl)cyclohexyl]aminocarbonyl]-4-methyl-2-[1-(phenylmethoxycarbonyl)-4-piperidyl]-1,3-thiazole 800 mg of 2-[(1H)-benzotriazol-1-yl]-1,1,3,3-tetramethyluronium tetrafluoroborate are added to a solution of 720 mg of 5-carboxy-4-methyl2-[1-(phenylmethoxycarbonyl)-4-piperidyl]-1,3-thiazole, 443 mg of methyl 3-(trans-4-aminocyclohexyl)propionate hydrochloride and 1.0 ml of triethylamine in 20 ml of dimethylformamide and the mixture is stirred at room temperature for 16 hours. The solvent is evaporated under reduced pressure and the residue is taken up in ethyl acetate. The organic phase is washed with water, 1M sodium hydroxide solution and saturated sodium chloride solution and dried, and the solvent is evaporated. The residue is chromatographed on silica gel using methylene chloride/methanol (50:1 to 30:1).

Yield: 980 mg (93% of theory),

Mass spectrum: $M^+$=527

$R_f$: 0.45 (silica gel; methylene chloride/methanol=15:1)

The following compounds are obtained analogously to Example 1:

(1) Methyl trans-3-[1-[1-(tert-butoxycarbonyl)-4-piperidyl]-4-imidazolyl]acrylate Methyl 4(5)-imidazolylacrylate is employed.

$R_f$: 0.55 (silica gel; methylene chloride/methanol/conc. ammonia=9:1:0.1)

(2) 2-[1-(tert-Butoxycarbonyl)-4-piperidyl]-5-[N-[trans-4-(2-methoxycarbonylethyl)cyclohexyl]-N-(3-pyridylmethyl)-aminocarbonyl]-1,3,4-thiadiazole Mass spectrum: $M^-$571

$R_f$: 0.56 (silica gel; methylene chloride/methanol/conc. ammonia=9:1:0.1)

(3) 2-[1-(tert-Butoxycarbonyl)-4-piperidyl]-5-[[trans-4-(2-methoxycarbonylethyl)cyclohexyl]aminocarbonyl]-1,3,4-thiadiazole Mass spectrum: $M^+$=480

$R_f$: 0.80 (silica gel; ethyl acetate/cyclohexane=4:1)

(4) 4-[[trans-4-(2-Methoxycarbonylethyl)cyclohexyl]aminocarbonyl]-2-[1-(phenylmethoxycarbonyl)-4-piperidyl]-1,3-thiazole Mass spectrum: $M^+$=346

$R_f$: 0.82 (silica gel; methylene chloride/methanol/conc. ammonia=4:1:0.25)

(5) 4-[[4-(Methoxycarbonylmethoxy)phenyl]aminocarbonyl]-2-[1-(phenylmethoxycarbonyl)-4-piperidyl]-1,3-thiazole $R_f$: 0.80 (silica gel; methylene chloride/methanol/conc. ammonia=4:1:0.25)

(6) 5-[[4-(Methoxycarbonylmethoxy)phenyl]aminocarbonyl]-4-methyl-2-[1-(phenylmethoxycarbonyl)-4-piperidyl]-1,3-thiazole $R_f$: 0.41 (silica gel; methylene chloride/methanol=15:1)

(7) 1-[1-(tert-Butoxycarbonyl)-4-piperidyl]-4-[[trans4-(2-methoxycarbonylethyl)cyclohexyl]-imidazole $R_f$: 0.39 (silica gel; methylene chloride/methanol=15:1)

(8) 1-[1-(tert-Butoxycarbonyl)-4-piperidyl]-4-[[4-(methoxycarbonylmethoxy)phenyl]aminocarbonyl]imidazole Mass spectrum: $M^+$=458

$R_f$: 0.41 (silica gel; methylene chloride/methanol=15:1)

(9) 1-[1-(tert-Butoxycarbonyl)-4-piperidyl]-4-[trans-2-[[trans-4-(methoxycarbonyl)cyclohexyl]aminocarbonyl]ethenyl]imidazole Melting point: 223°–224° C. (dec.)

Mass spectrum: $M^+$=460

$R_f$: 0.39 (silica gel; methylene chloride/methanol=15:1)

(10) 1-[1-(tert-Butoxycarbonyl)-4-piperidyl]-4-[trans-2-[[4-(methoxycarbonylmethyl)-1-piperidyl]carbonyl]ethenyl]imidazole Melting point: 159°–160° C. (dec.)

$R_f$: 0.47 (silica gel; methylene chloride/methanol/conc. ammonia=9:1:01)

(11) 2-[1-(tert-Butoxycarbonyl)-4-piperidyl]-5-[N-[trans-4-(2-methoxycarbonylethyl)cyclohexyl]-N-methylaminocarbonyl]-1,3,4-thiadiazole

(12) 2-[1-(tert-Butoxycarbonyl)-4-piperidyl]-5-[[1-(2-methoxycarbonylethyl)-4-piperidyl]aminocarbonyl]-1,3,4-thiadiazole

(13) 2-[1-(tert-Butoxycarbonyl)-4-piperidyl]-5-[[trans-4-[(methoxycarbonylmethyl)oxy]cyclohexyl]aminocarbonyl]-1,3,4-thiadiazole

(14) 2-[1-(tert-Butoxycarbonyl)-4-piperidyl]-5-[[1-(methoxycarbonylmethyl)-4-piperidyl]aminocarbonyl]-1,3,4-thiadiazole

(15) 2-[1-(tert-Butoxycarbonyl)-4-piperidyl]-5-[[[1-(methoxycarbonylmethyl)-4-piperidyl]methyl]aminocarbonyl]-1,3,4-thiadiazole

(16) 2-[4-(tert-Butoxycarbonyl)-1-piperazinyl]-5-[N-[4-(methoxycarbonylmethoxy)phenyl]-N-methylaminocarbonyl]-1,3,4-thiadiazole

(17) 2-[4-(tert-Butoxycarbonyl)-1-piperazinyl]-5-[[trans-4-(methoxycarbonylmethoxy)cyclohexyl]aminocarbonyl]-1,3,4-thiadiazole

(18) 2-[1-(tert-Butoxycarbonyl)-4-piperidyl]-5-[[4-[(2-methoxycarbonylethyl)oxy]-1-piperidyl]carbonyl]-1,3,4-thiadiazole

(19) 2-[1-(tert-Butoxycarbonyl)-4-piperidyl]-5-[[2-(4-methoxycarbonyl-1-piperidyl)ethyl]aminocarbonyl]-1,3,4-thiadiazole

(20) 2-[1-(tert-Butoxycarbonyl)-4-piperidyl]-5-[[4-(methoxycarbonylmethoxy)phenyl]carbonylamino]-1,3,4-thiadiazole

(21) 2-[1-(tert-Butoxycarbonyl)-4-piperidyl]-5-[[1-(2-methoxycarbonylethyl)-4-piperidyl]carbonylamino]-1,3,4-thiadiazole

(22) 5-[[4-[(2-Methoxycarbonylethyl)oxy]-1-piperidyl]carbonyl]-4-methyl-2-[1-(phenylmethoxycarbonyl)-4-piperidyl]-1,3-thiazole

(23) 1-[1-(tert-Butoxycarbonyl)-4-piperidyl]-4-[[1-(2-methoxycarbonylethyl)-4-piperidyl]carbonylamino]imidazole

(24) 1-[1-(tert-Butoxycarbonyl)-4-piperidyl]-4-[[[1-(methoxycarbonylmethyl)-4-piperidyl]methyl]carbonylamino]imidazole

(25) 5-[[4-(Methoxycarbonylmethoxy)phenyl]aminocarbonyl]-4-phenyl-2-[1-(phenylmethoxycarbonyl)-4-phenyl-2-[-1,3-thiazole

(26) 5-[[4-(Methoxycarbonylmethoxy)phenyl]aminocarbonyl]-4-methyl-2-[4-(phenylmethoxycarbonyl)-1-piperazinyl]-1,3-thiazole

(27) 5-[[4-(Methoxycarbonylmethoxy)phenyl]aminocarbonyl]-2-[1-(phenylmethoxycarbonyl)-4-piperidyl]-1,3-thiazole

(28) 2-[2-[1-(tert-Butoxycarbonyl)-4-piperidyl]ethyl]-4-methyl-5-[[trans-4-(methoxycarbonyl)cyclohexyl]aminocarbonyl]-1,3-thiazole

(29) 2-[[1-(tert-Butoxycarbonyl)-4-piperidyl]oxymethyl]-5-[[trans-4-(methoxycarbonyl)cyclohexyl]aminocarbonyl]-1,3-thiazole

(30) 2-[2-[1-(tert-Butoxycarbonyl)-4-piperidyl]ethyl]-5-[[trans-4-(methoxycarbonyl)cyclohexyl]aminocarbonyl]tetrazole

(31) 1-[2-[1-(tert-Butoxycarbonyl)-4-piperidyl]ethyl]-4-[N-[trans-4-(methoxycarbonyl)cyclohexyl]-N-phenylmethyl-aminocarbonyl]pyrazole

(32) 2-[1-(tert-Butoxycarbonyl)-4-piperidyl]-5-[[4-[2-(methoxycarbonyl)-2-(methanesulphonylamino)ethyl]phenyl]-aminocarbonyl]-1,3,4-oxadiazole

(33) 5-[[4-[2-(Methoxycarbonyl)ethyl]phenyl]aminocarbonyl]-4-methyl-2-[1-(phenylmethoxycarbonyl)-4-piperidyl]-1,3-thiazole
Melting point: 101°–104° C.
$R_f$: 0.20 (silica gel; methylene chloride/methanol/conc. ammonia=20:1:0.1)

(34) 5-[[[1-(tert-Butoxycarbonylmethyl)-4-piperidyl]methyl]aminocarbonyl]-4-methyl-2-[1-(phenylmethoxycarbonyl)-4-piperidyl]-1,3-thiazole
Mass spectrum: $M^+$=570
$R_f$: 0.15 (silica gel; methylene chloride/methanol/conc. ammonia=20:1:0.1)

(35) 1-[1-(tert-Butoxycarbonyl)-4-piperidyl]-4-[[2-(4ethoxycarbonyl-1-piperidyl)ethyl]aminocarbonyl]imidazole
Melting point: 166°–169° C.
Mass spectrum: $M^+$=477
$R_f$: 0.44 (silica gel; methylene chloride/methanol/conc. ammonia=9:1:0.1)

(36) 1-[1-(tert-Butoxycarbonyl)-4-piperidyl]-4-[4-[(2-methoxycarbonylethyl)oxy]piperidinocarbonyl]imidazole
Melting point: 184°–185° C.
Mass spectrum: $M^+$=464
$R_f$: 0.52 (silica gel; methylene chloride/methanol/conc. ammonia=9:1:0.1)

(37) 1-[2-[1-(tert-Butoxycarbonyl)-4-piperidyl]ethyl]-4-[[trans-4-(methoxycarbonyl)cyclohexyl]aminocarbonyl]imidazole
Methyl trans-4-aminocyclohexanecarboxylate hydrochloride is employed.
Melting point: 186° C.
$R_f$: 0.38 (silica gel; methylene chloride/methanol/conc. ammonia=9:1:0.1)

(38) 1-[2-[1-(tert-Butoxycarbonyl)-4-piperidyl]ethyl]-4-[[4-(methoxycarbonylmethyl)-1-piperazinyl]carbonyl]imidazole
Methyl piperazin-1-ylacetate dihydrochloride is employed.
Melting point: 142°–143° C.
$R_f$: 0.45 (silica gel; methylene chloride/methanol/conc. ammonia=9:1:0.1)

(39) 2-[2-[1-(Benzyloxycarbonyl)-4-piperidyl]ethyl]-4-methyl-5-[[trans-4-(methoxycarbonyl)cyclohexyl]aminocarbonyl]-1,3-thiazole
Methyl trans-4-aminocyclohexanecarboxylate is employed.
Melting point: 148°–151° C.
$R_f$: 0.53 (silica gel; methylene chloride/methanol/conc. ammonia=9:1:0.1)

(40) 2-[2-(1-(Benzyloxycarbonyl)-4-piperidyl]ethyl]-4-methyl-5-[[4-(methoxycarbonylmethyl)-1-piperazinylcarbonyl]-1,3-thiazole
Methyl piperazin-1-ylacetate dihydrochloride is employed.
Mass spectrum: $M^+$=528
$R_f$: 0.50 (silica gel; methylene chloride/methanol/conc. ammonia=9:1:0.1)

(41) 4-[[trans-4-(N-tert-Butoxycarbonylmethyl-N-methanesulphonylamino)cyclohexyl]carbonylamino]-1-(1-tert-butoxycarbonyl-4-piperidyl)imidazole trans-4-(N-tert-Butoxycarbonylmethyl-N-methanesulphonylamino)cyclohexanecarboxylic acid and 4-amino-1-[1-(tert-butoxycarbonyl)-4-piperidyl]imidazole are employed.
Mass spectrum: $M^+$=583
$R_f$: 0.45 (silica gel; methylene chloride/methanol/conc. ammonia=9:1:0.1)

(42) 5-[[trans-4-(2-Methoxycarbonylethyl)cyclohexyl]aminocarbonyl]-2-[1-(phenylmethoxycarbonyl)-4-piperidyl]-1,3-thiazole
The residue is triturated with ether and filtered off on a suction filter.
Mass spectrum: $M^+$=513
$R_f$: 0.36 (silica gel; methylene chloride/methanol=15:1)

(43) 5-[[4-(Cyclohexyloxycarbonylmethoxy)phenyl]aminocarbonyl]-2-[1-(phenylmethoxycarbonyl)-4-piperidyl]-1,3-thiazole
The amine component employed is hexyl α-(4-aminophenoxy)acetate.
The residue is triturated with ether and filtered off on a suction filter.
Mass spectrum: $M^+$=577
$R_f$: 0.51 (silica gel; methylene chloride/methanol=15:1)

(44) 5-[[trans-4-(tert-Butoxycarbonylmethoxy)cyclohexyl]aminocarbonyl]-2-[1-(phenylmethoxycarbonyl)-4-piperidyl]-1,3-thiazole
The residue is triturated with ether and filtered off on a suction filter.
Mass spectrum: $M^+$=557
$R_f$: 0.36 (silica gel; methylene chloride/methanol=15:1)

(45) 2-[2-(1-tert-Butoxycarbonyl-4-piperidyl)ethyl]-5-[[trans-4-(methoxycarbonyl)cyclohexyl]aminocarbonyl]-1,3-thiazole
Methyl trans-4-aminocyclohexanecarboxylate is employed.
$R_f$: 0.48 (silica gel; methylene chloride/methanol/conc. ammonia=9:1:0.1)

(46) 5-[1-(2-Methoxycarbonylethyl)-4-piperidyl]aminocarbonyl]-2-[1-(phenylmethoxycarbonyl)-4-piperidyl]-1,3-thiazole
The residue is triturated with methanol and filtered off on a suction filter.
Mass spectrum: $M^+$=514
$R_f$: 0.33 (silica gel; methylene chloride/methanol/conc. ammonia=9:1:0.1)

EXAMPLE 2

5-[[trans-4-(2-Methoxycarbonylethyl)cyclohexyl]aminocarbonyl]-4-methyl-2-(4-piperidyl)-1,3-thiazole hydrobromide A solution of 960 mg of 5-[[trans-4-(2-methoxycarbonylethyl)cyclohexyl]aminocarbonyl]-4-methyl-2-[1-(phenylmethoxycarbonyl)-4-piperidyl]-1,3- thiazole in 5 ml of glacial acetic acid and 5 ml of 33% strength hydrogen bromide in glacial acetic acid is stirred at room temperature for 2 hours. 50 ml of ether are added, the precipitate is filtered off on a suction filter, and the residue is triturated with acetone, filtered off on a suction filter again and dried in vacuo.

Yield: 900 mg (quantitative)

Mass spectrum: $M^+$=393

$R_f$: 0.09 (silica gel; methylene chloride/methanol/conc. ammonia=9:1:0.1)

The following compounds are obtained analogously to Example 2:

(1) 4-[[trans-4-(2-Methoxycarbonylethyl)cyclohexyl]aminocarbonyl]-2-(4-piperidyl)-1,3-thiazole hydrobromide Mass spectrum: $M^+$=379

$R_f$: 0.48 (silica gel; methylene chloride/methanol/conc. ammonia=4:1:0.25)

(2) 4-[[4-(Methoxycarbonylmethoxy)phenyl]aminocarbonyl]-2-(4-piperidyl)-1,3-thiazole hydrobromide Mass spectrum: $(M+H)^+$=376

$R_f$: 0.50 (silica gel; methylene chloride/methanol/conc. ammonia=4:1:0.25)

(3) 5-[[4-(Methoxycarbonylmethoxy)phenyl]aminocarbonyl]-4-methyl-2-(4-piperidyl)-1,3-thiazole hydrobromide Mass spectrum: $M^+$=389

$R_f$: 0.41 (silica gel; methylene chloride/methanol=15:1)

(4) 5-[[4-[(2-Methoxycarbonylethyl)oxy]-1-piperidyl]carbonyl]-4-methyl-2-(4-piperidyl)-1,3-thiazole hydrobromide (5) 5-[[4-(Methoxycarbonylmethoxy)phenyl]aminocarbonyl]-4-phenyl-2-(4-piperidyl)-1,3-thiazole hydrobromide (6) 5-[[4-(Methoxycarbonylmethoxy)phenyl]aminocarbonyl]-4-methyl-2-(1-piperazinyl)-1,3-thiazole hydrobromide (7) 5-[[4-(Methoxycarbonylmethoxy)phenyl]aminocarbonyl]-2-(4-piperidyl)-1,3-thiazole hydrobromide (8) 5-[[4-[2-(Methoxycarbonyl)ethyl]phenyl]aminocarbonyl]-4-methyl-2-(4-piperidyl)-1,3-thiazole hydrobromide Mass spectrum: $M^+$=387

$R_f$: 0.69 (silica gel; methylene chloride/methanol/conc. ammonia=4:1:0.2)

(9) 5-[[[1-(Carboxymethyl)-4-piperidyl]methyl]aminocarbonyl]-4-methyl-2-(4-piperidyl)-1,3-thiazole dihydrobromide The starting material employed is 5-[[[1-(tert-butoxycarbonylmethyl)-4-piperidyl]methyl]aminocarbonyl]-4-methyl-2-[1-(phenylmethoxycarbonyl)-4-piperidyl]-1,3-thiazole.

Mass spectrum: $M^+$=380

$R_f$: 0.13 (silica gel; methylene chloride/methanol/conc. ammonia=2:1:0.25)

(10) 5-[[trans-4-(2-Methoxycarbonylethyl)cyclohexyl]aminocarbonyl]-2-(4-piperidyl)-1,3-thiazole hydrobromide Mass spectrum: $M^+$=379

$R_f$: 0.66 (silica gel; methylene chloride/methanol/conc. ammonia=4:1:0.25)

(11) 5-[[4-(Cyclohexyloxycarbonylmethoxy)phenyl]aminocarbonyl]-2-(4-piperidyl)-1,3-thiazole hydrobromide The residue is triturated with ether and filtered off on a suction filter.

Mass spectrum: $M^+$=443

$R_f$: 0.64 (silica gel; methylene chloride/methanol/conc. ammonia=4:1:0.25)

(12) 5-[[trans-4-(Carboxymethoxy)cyclohexyl]aminocarbonyl]-2-(4-piperidyl)-1,3-thiazole hydrobromide 5-[[trans-4-(tert-butoxycarbonylmethoxy)cyclohexyl]aminocarbonyl]-2-[1-(phenylmethoxycarbonyl)-4-piperidyl]-1,3-thiazole is employed.

Melting point: 197° C. (sintering)

Mass spectrum: $(M+H)^+$=368

$R_f$: 0.38 (silica gel; methylene chloride/methanol/conc. ammonia=2:1:0.25)

(13) 5-[[1-(2-Methoxycarbonylethyl)-4-piperidyl]aminocarbonyl]-2-(4-piperidyl)-1,3-thiazole dihydrobromide Melting point: from 240° C. (sintering)

Mass spectrum: $(M+H)^+$=381

$R_f$: 0.42 (silica gel; methylene chloride/methanol/conc. ammonia=4:1:0.2)

(14) 5-[[4-(Ethoxycarbonylmethoxy)phenyl]oxymethyl]-2-[4-piperidyl]-1,3,4-thiadiazole hydrobromide Melting point: 168°–179° C.

Mass spectrum: $M^+$=377

$R_f$: 0.35 (silica gel; methylene chloride/methanol/conc. ammonia=9:1:0.1)

(15) 5-[2-[4-(Ethoxycarbonylmethoxy)phenyl]ethyl]-2-[4-piperidyl]-1,3,4-thiadiazole hydrobromide Melting point: 183°–184° C.

Mass spectrum: $M^+$=375

$R_f$: 0.24 (silica gel; methylene chloride/methanol/conc. ammonia=9:1:0.1)

EXAMPLE 3

4-[[trans-4-(2-Methoxycarbonylethyl)cyclohexyl]aminocarbonyl]-1-(4-piperidyl)imidazole dihydrochloride A solution of 420 mg 1-[1-(tert-butoxycarbonyl)-4-piperidyl]-4-[[trans-4-(2-methoxycarbonylethyl)cyclohexyl]aminocarbonyl]imidazole in 10 ml of methanol and 10 ml of ethereal hydrochloric acid is stirred at room temperature for 16 hours. The solvent is evaporated under reduced pressure, and the residue is triturated with ether and filtered off on a suction filter.

Yield: 390 mg (quantitative), mass spectrum: $M^+$=362

$R_f$: 0.09 (silica gel; methylene chloride/methanol/conc. ammonia=9:1:0.1)

The following compounds are obtained analogously to Example 3:

(1) 4-[[4-(Methoxycarbonylmethoxy)phenyl]aminocarbonyl]-1-(4-piperidyl)imidazole dihydrochloride Mass spectrum: $M^+$=358

$R_f$: 0.15 (silica gel; methylene chloride/methanol/conc. ammonia=9:1:0.1)

(2) 5-[[trans-4-(2-Methoxycarbonylethyl)cyclohexyl]aminocarbonyl]-2-(4-piperidyl)-1,3,4-thiadiazole hydrochloride The reaction is carried out in a solvent mixture of dioxane/methanol/ethereal hydrochloric acid (1:1:1). The mixture is stirred at room temperature for 30 minutes.

Melting point: 211°–215° C.

Mass spectrum: $M^+$=380

$R_f$: 0.14 (silica gel; methylene chloride/methanol/conc. ammonia=4:1:0.2)

(3) 4-[trans-2-[[trans-4-(Methoxycarbonyl)cyclohexyl]aminocarbonyl]ethenyl]-1-(4-piperidyl)imidazole dihydrochloride Mass spectrum: M$^+$=360

R$_f$: 0.11 (silica gel; methylene chloride/methanol/conc. ammonia=9:1:0.1)

(4) 4-[trans-2-[[4-(Methoxycarbonylmethyl)-1-piperazinyl]-carbonyl]ethenyl]-1-(4-piperidyl)imidazole trihydrochloride Melting point: 159°–160° C. (dec.)

Mass spectrum: M$^+$=361

R$_f$: 0.44 (silica gel; methylene chloride/methanol/conc. ammonia=4:1:0.25)

(5) 5-[N-[trans-4-(2-Methoxycarbonylethyl)cyclohexyl]-N-methylaminocarbonyl]-2-(4-piperidyl)-1,3,4-thiadiazole hydrochloride (6) 5-[[1-(2-Methoxycarbonylethyl)-4-piperidyl]aminocarbonyl]-2-(4-piperidyl)-1,3,4-thiadiazole dihydrochloride (7) 5-[[trans-4-[(Methoxycarbonylmethyl)oxy]cyclohexyl]aminocarbonyl]-2-(4-piperidyl)-1,3,4-thiadiazole hydrochloride (8) 5-[[1-(Methoxycarbonylmethyl)-4-piperidyl]aminocarbonyl]-2-(4-piperidyl)-1,3,4-thiadiazole dihydrochloride (9) 5-[[[1-(Methoxycarbonylmethyl)-4-piperidyl]methyl]aminocarbonyl]-2-(4-piperidyl)-1,3,4-thiadiazole dihydrochloride

(10) 5-N-[4-(Methoxycarbonylmethoxy)phenyl]-N-methylaminocarbonyl]-2-(1-piperazinyl)-1,3,4-thiadiazole dihydrochloride

(11) 5-[[trans-4-(Methoxycarbonylmethoxy)cyclohexyl]aminocarbonyl]-2-(1-piperazinyl)-1,3,4-thiadiazole dihydrochloride

(12) 5-[[4-[(2-Methoxycarbonylethyl)oxy]-1-piperidyl]carbonyl]-2-(4-piperidyl)-1,3,4-thiadiazole hydrochloride

(13) 5-[[2-(4-Methoxycarbonyl-1-piperidyl)ethyl]aminocarbonyl]-2-(4-piperidyl)-1,3,4-thiadiazole dihydrochloride

(14) 5-[[4-(Methoxycarbonylmethoxy)phenyl]carbonylamino]-2-(4-piperidyl)-1,3,4-thiadiazole hydrochloride

(15) 5-[[1-(2-Methoxycarbonylethyl)-4-piperidyl]carbonylamino]-2-(4-piperidyl)-1,3,4-thiadiazole dihydrochloride

(16) 4-[[1-(2-Methoxycarbonylethyl)-4-piperidyl]carbonylamino]-1-(4-piperidyl)imidazole trihydrochloride

(17) 4-[[[1-(Methoxycarbonylmethyl)-4-piperidyl]methyl]carbonylamino]-1-(4-piperidyl)imidazole trihydrochloride

(18) 5-[[trans-4-(Methoxycarbonyl)cyclohexyl]aminocarbonyl]-4-methyl-2-[2-(4-piperidyl)ethyl]-1,3-thiazole hydrochloride

(19) 5-[[trans-4-(Methoxycarbonyl)cyclohexyl]aminocarbonyl]-2-[(4-piperidyl)oxymethyl]-1,3-thiazole hydrochloride

(20) 5-[[trans-4-(Methoxycarbonyl)cyclohexyl]aminocarbonyl]-2-[2-(4-piperidyl)ethyl]tetrazole hydrochloride

(21) 4-[N-[trans-4-(Methoxycarbonyl)cyclohexyl]-N-phenylmethylaminocarbonyl]-1-[2-(4-piperidyl)ethyl]pyrazole hydrochloride

(22) 5-[[4-[2-(Methoxycarbonyl)-2-(methanesulphonylamino)-ethyl]phenyl]aminocarbonyl]-2-(4-piperidyl)-1,3,4-oxadiazole hydrochloride

(23) 4-[[2-(4-Methoxycarbonyl-1-piperidyl)ethyl]aminocarbonyl]-1-(4-piperidyl)imidazole trihydrochloride The starting material employed is compound 35 of Example 1. Transesterification takes place under the reaction conditions.

Mass spectrum: M$^+$=363

R$_f$: 0.60 (silica gel; methylene chloride/methanol/conc. ammonia=4:1:0.25)

(24) 4-[4-[(2-Methoxycarbonylethyl)oxy]piperidinocarbonyl]-1-(4-piperidyl)imidazole dihydrochloride Mass spectrum: M$^+$=364

R$_f$: 0.11 (silica gel; methylene chloride/methanol/conc. ammonia=9:1:0.1)

(25) 1-[2-(4-Piperidyl)ethyl]-4-[[trans-4-(methoxycarbonyl)-cyclohexyl]aminocarbonyl]imidazole dihydrochloride The mixture is stirred at room temperature for 2 hours.

Mass spectrum: M$^+$=362

R$_f$: 0.35 (silica gel; methylene chloride/methanol/conc. ammonia=4:1:0.25)

(26) 1-[2-(4-Piperidyl)ethyl]-4-[[4-(methoxycarbonylmethyl)-1-piperazinyl]carbonyl]imidazole trihydrochloride The mixture is stirred at room temperature for 2 hours.

Mass spectrum: M$^+$=363

R$_f$: 0.33 (silica gel; methylene chloride/methanol/conc. ammonia=4:1:0.25)

(27) 5-[[trans-4-(Methoxycarbonyl)cyclohexyl]aminocarbonyl]-2-[2-(4-piperidyl)ethyl]-1,3-thiazole The reaction is carried out in a solvent mixture of dioxane/methanol/methanolic hydrochloric acid (1:1:1).

Melting point: 219°–225° C. (sintering)

Mass spectrum: M$^+$=379

R$_f$: 0.61 (silica gel; methylene chloride/methanol/conc. ammonia=2:1:0.2)

EXAMPLE 4

4-[[trans-4-(2-Carboxyethyl)cyclohexyl]aminocarbonyl]-1-(4-piperidyl)imidazole dihydrochloride A solution of 225 mg of 4-([trans-4-(2-methoxycarbonylethyl)cyclohexyl]aminocarbonyl]-1-(4-piperidyl)imidazole dihydrochloride in 10 ml of 6M hydrochloric acid is stirred at room temperature for 16 hours. The solvent is evaporated under reduced pressure, and the residue is triturated with acetone and filtered off on a suction filter.

Yield: 200 mg (92% of theory),

Mass spectrum: M$^+$=348

R$_f$: 0.39 (silica gel; methylene chloride/methanol/conc. ammonia=2:1:0.25)

The following compounds are obtained analogously to Example 4:

(1) 4-[[4-(Carboxymethoxy)phenyl]aminocarbonyl]-1-(4-piperidyl)imidazole dihydrochloride Mass spectrum: M$^+$=344

R$_f$: 0.18 (silica gel; methylene chloride/methanol/conc. ammonia=2:1:0.25)

(2) 5-[[trans-4-(2-Carboxyethyl)cyclohexyl]aminocarbonyl]-4-methyl-2-(4-piperidyl)-1,3-thiazole hydrobromide The starting material employed is the compound of Example 2.

Mass spectrum: M$^+$=348

R$_f$: 0.39 (silica gel; methylene chloride/methanol/conc. ammonia=2:1:0.25)

(3) 5-[[4-(Carboxymethoxy)phenyl]aminocarbonyl]-4-methyl- 2-(4-piperidyl)-1,3-thiazole hydrobromide The starting material employed is compound 3 of Example 2; it is recrystallized from water/ethanol.
Melting point: 235° C. (decomposition)
Mass spectrum: M$^+$=379
R$_f$: 0.33 (silica gel; methylene chloride/methanol/conc. ammonia=2:1:0.25)

(4) 4-[[4-(Carboxymethoxy)phenyl]aminocarbonyl]-2-(4-piperidyl)-1,3-thiazole hydrobromide
The starting material employed is compound 2 of Example 2, the residue is triturated with ether.
Mass spectrum: (M+H)$^+$=362
R$_f$: 0.51 (silica gel; methylene chloride/methanol/conc. ammonia=2:1:0.25)

(5) 5-[[trans-4-(2-Carboxyethyl)cyclohexyl]aminocarbonyl]-2-(4-piperidyl)-1,3,4-thiadiazole hydrochloride
The mixture is stirred at room temperature for 3 hours. The residue is triturated with ether.
Mass spectrum: M$^+$=366
R$_f$: 0.42 (silica gel; methylene chloride/methanol/conc. ammonia=2:1:0.2)

(6) 5-[[4-(Carboxymethoxy)phenyl]aminocarbonyl]-2-(4piperidyl)-1,3,4-thiadiazole hydrochloride
Melting point: 310°–315° C. (dec.)
Mass spectrum: (M+H)$^+$=363
R$_f$: 0.14 (silica gel; methylene chloride/methanol conc. ammonia=2:1:0.2)

(7) 5-[N-[trans-4-(2-Carboxyethyl)cyclohexyl]-N-(3-pyridylmethyl)aminocarbonyl]-2-(4-piperidyl)-1,3,4-thiadiazole dihydrochloride
The mixture is stirred at room temperature for 3 hours. The solvent is evaporated under reduced pressure and the residue is dried in vacuo.
Mass spectrum: M$^{+=457}$
R$_f$: 0.28 (silica gel; methylene chloride/methanol/conc. ammonia=2:1:0.2)

(8) 4-[trans-2-[(trans-4-Carboxycyclohexyl)aminocarbonyl]-ethenyl]-1-(4-piperidyl)imidazole dihydrochloride
Mass spectrum: M$^+$=346
R$_f$: 0.24 (silica gel; methylene chloride/methanol/conc. ammonia=2:1:0.25)

(9) 4-[2-[(trans-4-Carboxycyclohexyl)aminocarbonyl]ethyl]-1-(4-piperidyl)imidazole dihydrochloride
Mass spectrum: M$^+$=348
R$_f$: 0.23 (silica gel; methylene chloride/methanol/conc. ammonia=2:1:0.25)

(10) 5-[N-[trans-4-(2-Carboxyethyl)cyclohexyl]-N-methylaminocarbonyl]-2-(4-piperidyl)-1,3,4-thiadiazole hydrochloride

(11) 5-[[trans-4-(Carboxymethoxy)cyclohexyl]aminocarbonyl]-2-(4-piperidyl)-1,3,4-thiadiazole hydrochloride

(12) 5-[N-[4-Carboxymethoxy)phenyl]-N-methylaminocarbonyl]-2-(1-piperazinyl)-1,3,4-thiadiazole dihydrochloride

(13) 5-[[trans-4-(Carboxymethoxy)cyclohexyl]aminocarbonyl]-2-(1-piperazinyl)-1,3,4-thiadiazole dihydrochloride

(14) 5-[[4-[(2-Carboxyethyl)oxy]-1-piperidyl]carbonyl]-2-(4-piperidyl)-1,3,4-thiadiazole hydrochloride

(15) 5-([4-(Carboxymethoxy)phenyl]carbonylamino]-2-(4-piperidyl)-1,3,4-thiadiazole hydrochloride

(16) 5-[[4-[(2-Carboxyethyl)oxy]-1-piperidyl]carbonyl]-4-methyl-2-(4-piperidyl)-1,3-thiazole hydrobromide The starting material employed is the compound of Example 2(4).

(17) 5-[[4-(Carboxymethoxy)phenyl]aminocarbonyl]-4-phenyl-2-(4-piperidyl)-1,3-thiazole hydrobromide The starting material employed is the compound of Example 2(5).

(18) 5-[[4-(Carboxymethoxy)phenyl]aminocarbonyl]-4-methyl-2-(1-piperazinyl)-1,3-thiazole dihydrobromide
The starting material employed is the compound of Example 2(6).

(19) 5-[[4-(Carboxymethoxy)phenyl]aminocarbonyl]-2-(4-piperidyl)-1,3-thiazole hydrate
The starting material employed is 5-[[4-(cyclohexyloxycarbonylmethoxy)phenyl]aminocarbonyl]-2-(4-piperidyl)-1,3-thiazole hydrobromide. The product is recrystallized from dilute sodium chloride solution.
Melting point: 365° C. (dec.)
Mass spectrum: (M+H)$^+$362
R$_f$: 0.28 (silica gel; methylene chloride/methanol/conc. ammonia=2:1:0.25)

(20) 5-[[trans-4-(2-Carboxyethyl)cyclohexyl]aminocarbonyl]-2-(4-piperidyl)-1,3-thiazole hydrobromide The starting material employed is the compound of Example 2(10).
Melting point: 245°–247° C. (sintering)
Mass spectrum: M$^+$=365
R$_f$: 0.44 (silica gel; methylene chloride/methanol/conc. ammonia=2:1:0.25)

(21) 5-[(trans-4-(Carboxy)cyclohexyl]aminocarbonyl]-2-[(4-piperidyl)oxymethyl]-1,3-thiazole hydrochloride

(22) 5-[[trans-4-(Carboxy)cyclohexyl]aminocarbonyl]-2-[2-(4-piperidyl)ethyl]tetrazole hydrochloride

(23) 4-[N-[trans-4-(Carboxy)cyclohexyl]-N-phenylmethylaminocarbonyl]-1-[2-(4-piperidyl)ethyl]pyrazole hydrochloride

(24) 5-[[4-[2-(Carboxy)-2-(methanesulphonylamino)ethyl]phenyl]aminocarbonyl]-2-(4-piperidyl)-1,3,4-oxadiazole hydrochloride

(25) 4-[[2-(4-Carboxy-1-piperidyl)ethyl]aminocarbonyl]-1-(4-piperidyl)imidazole trihydrochloride
Mass spectrum: (M+H)$^+$=350
R$_f$: 0.12 (silica gel; methylene chloride/methanol/conc. ammonia=2:1:0.25)

(26) 4-[4-[(2-Carboxyethyl)oxy]piperidinocarbonyl]-1-(4-piperidyl)imidazole dihydrochloride
Mass spectrum: M$^+$=350
R$_f$: 0.21 (silica gel; methylene chloride/methanol/conc. ammonia=2:1:0.25)

(27) 4-[[trans-4-Carboxycyclohexyl]aminocarbonyl]-1-[2-(4-piperidyl)ethyl]imidazole dihydrochloride
Mass spectrum: M$^+$=348
R$_f$: 0.13 (silica gel; methylene chloride/methanol/conc. ammonia=2:1:0.25)

(28) 5-[[4-(Carboxymethoxy)phenyl]oxymethyl]-2-[4-piperidyl]-1,3,4-thiadiazole hydrochloride
The starting material employed is compound 14 of Example 2. The mixture is stirred at room temperature for 4 hours. The crystalline precipitate is filtered off on a suction filter and dried. The compound crystallizes in the form of the hydrochloride.
Melting point: 275°–277° C.
Mass spectrum: (M+H)$^+$=350
R$_f$: 0.06 (silica gel; methylene chloride/methanol/conc. ammonia=4:1:0.2)

(29) 5-[2-[4-(Carboxymethoxy)phenyl]ethyl]-2-[4-piperidyl]-1,3,4-thiadiazole hydrobromide
The starting material employed is compound 15 of Example 2. The mixture is stirred at room temperature for 4 hours.
Melting point: 261°–264° C.
Mass spectrum: (M+H)$^+$=348
R$_f$: 0.14 (silica gel; methylene chloride/methanol/conc. ammonia=4:1:0.2)

EXAMPLE 5

5-[[4-(Methoxycarbonylmethoxy)phenyl]aminocarbonyl]-2-(4-piperidyl)-1,3,4-thiadiazole trifluoroacetate 5 ml of trifluoroacetic acid are added at 0° C. to a solution of 390 mg of 2-[1-(tert-butoxycarbonyl)-4-piperidyl]-5-[[4-(methoxycarbonylmethoxy)phenyl]aminocarbonyl]-1,3,4-thiadiazole. The mixture is stirred at room temperature for 1.5 hours and evaporated under reduced pressure. The residue is triturated with a little anhydrous methanol and filtered off on a suction filter.

Yield: 120 mg (44% of theory),

Mass spectrum: $(M+H)^+ = 377$ $R_f$: 0.11 (silica gel; methylene chloride/methanol/conc. ammonia 9:1:0.1)

The following compounds are obtained analogously to Example 5.

(1) 5-[N-[trans-4-(2-Methoxycarbonylethyl)cyclohexyl]-N-(3-pyridylmethyl)aminocarbonyl]-2-(4-piperidyl)-1,3,4-thiadiazole dihydrochloride The residue is dissolved in ethyl acetate and extracted with 0.5M sodium hydroxide solution. The organic phase is dried and evaporated. The residue is dissolved in anhydrous methanol and acidified with ethereal hydrochloric acid, and the solvent is evaporated under reduced pressure.

Mass spectrum: $(M+H)^+ = 472$ $R_f$: 0.24 (silica gel; methylene chloride/methanol/conc. ammonia=9:1:0.1)

(2) 4-[[trans-4-(N-Carboxymethyl-N-methanesulphonylamino)-cyclohexyl]carbonylamino]-1-(4-piperidyl)imidazole dihydrochloride 4-[[trans-4-(N-tert-Butoxycarbonylmethyl-N-methanesulphonyl-amino)cyclohexyl]carbonylamino]-1-(1-tert-butoxycarbonyl-4-piperidyl)imidazole is employed. By dissolving in 1N hydrochloric acid and evaporating the solvent, the hydrochloride is prepared.

Mass spectrum: $(M+H)^+ = 428$ $R_f$: 0.34 (silica gel; methylene chloride/methanol/conc. ammonia=2:1:0.25)

(3) 4-[[4-(Methoxycarbonylmethoxy)phenyl]carbonylamino]-1-(4-piperidyl)imidazole dihydrochloride The residue is dissolved in methanol. Ethereal hydrochloric acid is added and the mixture is evaporated. The product is triturated with acetone and filtered off on a suction filter.

Mass spectrum: $M^+ = 358$ $R_f$: 0.18 (silica gel; methylene chloride/methanol/conc. ammonia=9:1:0.1)

EXAMPLE 6

4-[[trans-4-(2-Carboxyethyl)cyclohexyl]aminocarbonyl]-2-(4-piperidyl)-1,3-thiazole Sufficient methanol such that a clear solution results is added to a suspension of 180 mg of 4-[[trans-4-(2-methoxycarbonylethyl)cyclohexyl]aminocarbonyl]-2-(4-piperidyl)-1,3-thiazole hydrobromide in 10 ml of tetrahydrofuran. 2 ml of sodium hydroxide solution are added, and the mixture is stirred at room temperature for 6 hours and neutralized with 1M hydrochloric acid. The solvents are evaporated under reduced pressure and the residue is chromatographed on silica gel using methylene chloride/methanol/conc. ammonia=2:1:0.25.

Yield: 200 mg (product contains inorganic salts),

Mass spectrum: $M^+ = 365$ $R_f$: 0.54 (silica gel; methylene chloride/methanol/conc. ammonia=2:1:0.25)

The following compounds are obtained analogously to Example 6:

(1) 4-[trans-2-[[4-(Carboxymethyl)-1-piperazinyl]carbonyl]ethenyl]-1-(4-piperidyl)imidazole Mass spectrum: $M^+ = 347$ $R_f$: 0.27 (silica gel; methylene chloride/methanol/conc. ammonia=2:1:0.25)

(2) 4-[2-[[4-(Carboxymethyl)-1-piperazinyl]carbonyl]ethyl]-1-(4-piperidyl)imidazole Mass spectrum: $(M+H)^+ = 350$ $R_f$: 0.09 (silica gel; methylene chloride/methanol/conc. ammonia=2:1:0.25)

(3) 5-[[1-(2-Carboxyethyl)-4-piperidyl]aminocarbonyl]-2-(4-piperidyl)-1,3,4-thiadiazole (4) 5-[[1-(Carboxymethyl)-4-piperidyl]aminocarbonyl]-2-(4-piperidyl)-1,3,4-thiadiazole (5) 5-[[1-(Carboxymethyl)-4-piperidyl]methylaminocarbonyl]-2-(4-piperidyl)-1,3,4-thiadiazole (6) 5-[[2-(4-Carboxy-1-piperidyl)ethyl]aminocarbonyl]-2-(4-piperidyl)-1,3,4-thiadiazole (7) 5-[[1-(2-Carboxyethyl)-4-piperidyl]carbonylamino]-2-(4-piperidyl)-1,3,4-thiadizole (8) 4-[[1-(2-Carboxyethyl)-4-piperidyl]carbonylamino]-1-(4-piperidyl)imidazole (9) 4-[[[1-(Carboxymethyl)-4-piperidyl]methyl]carbonylamino]-1-(4-piperidyl)imidazole

(10) 5-[[4-(2-Carboxyethyl)phenyl]aminocarbonyl]-4-methyl-2-(4-piperidyl)-1,3-thiazole The hydrolysis is carried out using lithium hydroxide in tetrahydrofuran/water (5:4).

Melting point: 286°–289° C.

Mass spectrum: $M^+ = 373$ $R_f$: 0.27 (silica gel; methylene chloride/methanol/conc. ammonia=2:1:0.2)

(11) 1-[2-(4-Piperidyl)ethyl]-4-[[4-(carboxymethyl)-1-piperazinyl]carbonyl]imidazole The residue is stirred with methylene chloride/absolute methanol (1:1) and filtered off on a suction filter. The filtrate is evaporated.

Mass spectrum: $(M+H)^+ = 350$ $R_f$: 0.09 (silica gel; methylene chloride/methanol/conc. ammonia=2:1:0.25)

(12) 5-[(trans-4-Carboxycyclohexyl)aminocarbonyl]-4-methyl-2-[2-(4-piperidyl)ethyl]-1,3-thiazole hydrochloride The hydrolysis is carried out using lithium hydroxide in tetrahydrofuran/water (5:4). After 4 hours, the mixture is acidified with 1N hydrochloric acid and excess tetrahydrofuran is evaporated. The precipitate is filtered off on a suction filter and washed with a little water.

Melting point: 285°–295° C. (dec.)

Mass spectrum: $M^+ = 379$ $R_f$: 0.16 (silica gel; methylene chloride/methanol/conc. ammonia=2:1:0.2)

(13) 5-[[4-(Carboxymethyl)-1-piperazinyl]carbonyl]-4-methyl-2-[2-(4-piperidyl)ethyl]-1,3-thiazole The hydrolysis is carried out using lithium hydroxide in tetrahydrofuran/water (5:4). After 4 hours, the solvent is evaporated under reduced pressure and the crude product is chromatographed on silica gel using methylene chloride/methanol/conc. ammonia (2:1:0.2).

Mass spectrum: $M^+ = 381$ $R_f$: 0.16 (silica gel; methylene chloride/methanol/conc. ammonia=2:1:0.2)

(14) 4-[[4-(Carboxymethoxy)phenyl]carbonylamino]-1-(4-piperidyl)imidazole

The organic solvent is evaporated and the aqueous solution is cooled. The precipitate is filtered off on a suction filter.

Mass spectrum: M⁺=344

$R_f$: 0.21 (silica gel; methylene chloride/methanol/conc. ammonia=2:1:0.25)

(15) 5-[(trans-4-Carboxycyclohexyl)aminocarbonyl]-2-[2-(4-piperidyl)ethyl]-1,3-thiazole hydrochloride The hydrolysis is carried out using lithium hydroxide in tetrahydrofuran/water (5:4). After 5 hours, the mixture is acidified with 1N hydrochloric acid.

Melting point: 279°–284° C.

Mass spectrum: M⁺=365

$R_f$: 0.17 (silica gel; methylene chloride/methanol/conc. ammonia=2:1:0.2)

(16) 5-[(1-(2-Carboxyethyl)-4-piperidyl]aminocarbonyl]-2-(4-piperidyl)-1,3-thiazole The hydrolysis is carried out using lithium hydroxide in tetrahydrofuran/water (5:4). The crude product is chromatographed on silica gel using methylene chloride/methanol/conc. ammonia (2:1:0.2).

Melting point: 280°–285° C.

Mass spectrum: M⁺=366

$R_f$: 0.15 (silica gel; methylene chloride/methanol/conc. ammonia=2:1:0.2)

EXAMPLE 7

4-[2-[[trans-4-(Methoxycarbonyl)cyclohexyl]aminocarbonyl]-ethyl]-1-(4-piperidyl)imidazole dihydrochloride A solution of 770 mg of 4-[trans-2-[[trans-4-(methoxycarbonyl)cyclohexyl]aminocarbonyl]ethenyl]-1-(4-piperidyl)-imidazole dihydrochloride in 25 ml of methanol is hydrogenated in the presence of 0.2 g of 10% strength palladium on carbon at a hydrogen pressure of 3 bar and at a temperature of 40° C. The catalyst is filtered off and the solvent is evaporated under reduced pressure.

Yield: 730 mg (94% of theory),

Mass spectrum: M⁺=362

$R_f$: 0.51 (silica gel; methylene chloride/methanol/conc. ammonia=4:1:0.25)

The following compounds are obtained analogously to Example 7:

(1) 4-[2-[[4-(Methoxycarbonylmethyl)-1-piperazinyl]carbonyl]ethyl]-1-(4-piperidyl)imidazole trihydrochloride Mass spectrum: M⁺=363

$R_f$: 0.44 (silica gel; methylene chloride/methanol/conc. ammonia=4:1:0.25)

(2) 5-[[trans-4-(Methoxycarbonyl)cyclohexyl]aminocarbonyl]-4-methyl-2-[2-(4-piperidyl)ethyl]-1,3-thiazole 2-[2-[1-(Benzyloxycarbonyl)-4-piperidyl]ethyl]-4-methyl-5-[[trans-4-(methoxycarbonyl)cyclohexyl]aminocarbonyl]-1,3-thiazole is hydrogenated at room temperature. The crude product is chromatographed on silica gel using methylene chloride/methanol/conc. ammonia (4:1:0.2).

Melting point: 168°–170° C.

Mass spectrum: M⁺=393

$R_f$: 0.19 (silica gel; methylene chloride/methanol/conc. ammonia=4:1:0.2)

(3) 5-[[4-(Methoxycarbonylmethyl)-1-piperazinyl]carbonyl]-4-methyl-2-[2-(4-piperidyl)ethyl]-1,3-thiazole 2-[2-[1-(Benzyloxycarbonyl)-4-piperidyl]ethyl]-4-methyl-5-[[4-(methoxycarbonylmethyl)-1-piperazinyl]carbonyl]-1,3-thiazole is hydrogenated at room temperature. The crude product is chromatographed on silica gel using methylene chloride/methanol/conc. ammonia (4:1:0.2).

Mass spectrum: M⁺=394

$R_f$: 0.22 (silica gel; methylene chloride/methanol/conc. ammonia=4:1:0.2)

EXAMPLE 8

5-[[4-(Cyclohexyloxycarbonylmethoxy)phenyl]aminocarbonyl]-4-methyl-2-(4-piperidyl)-1,3-thiazole hydrochloride A solution of 150 mg of 5-[[4-(carboxymethoxy)phenyl]aminocarbonyl]-4-methyl-2-(4-piperidyl)-1,3-thiazole hydrochloride in 15 g of cyclohexanol and 10 ml of ethereal hydrochloric acid is heated at reflux for 1 hour. The ether is distilled off and the reaction solution is stirred at 60° C. for 4 hours. The cyclohexanol is evaporated under reduced pressure, and the residue is triturated with ether and filtered off on a suction filter.

Yield: 135 mg (75% of theory),

Mass spectrum: M⁺=457

$R_f$: 0.80 (silica gel; methylene chloride/methanol=2:1:0.25)

The following compounds are obtained analogously to Example 8:

(1) 5-[[[1-(Methoxycarbonylmethyl)-4-piperidyl]methyl]aminocarbonyl]-4-methyl-2-(4-piperidyl)-1,3-thiazole hydrochloride The reaction is carried out in methanol/ethereal hydrochloric acid (3:1). The mixture is stirred at room temperature for 16 hours.

Mass spectrum: (M+H)⁺=395

$R_f$: 0.77 (silica gel; methylene chloride/methanol/conc. ammonia=4:1:0.2)

(2) 5-[[trans-4-(Ethoxycarbonylmethoxy)cyclohexyl]aminocarbonyl]-2-(4-piperidyl)-1,3-thiazole hydrochloride The reaction is carried out in ethanol/ethereal hydrochloric acid (2:1). The mixture is stirred at room temperature for 16 hours.

Mass spectrum: M⁺=395

$R_f$: 0.82 (silica gel; methylene chloride/methanol/conc. ammonia=2:1:0.25)

(3) 5-[[4-(Ethoxycarbonylmethoxy)phenyl]aminocarbonyl]-2-(4-piperidyl)-1,3-thiazole hydrochloride The reaction is carried out in ethanol/ethereal hydrochloric acid (2:1). The mixture is stirred at room temperature for 16 hours. It is then heated under reflux for 5 hours.

Mass spectrum: M⁺=389

$R_f$: 0.70 (silica gel; methylene chloride/methanol/conc. ammonia=2:1:0.25)

(4) 5-[(4-(Isopropoxycarbonylmethoxy)phenyl]aminocarbonyl]-2-(4-piperidyl)-1,3,4-thiadiazole hydrochloride The reaction is carried out in isopropanol/ethereal hydrochloric acid (6:1). After evaporation of the ether, the mixture is heated at 80° C. for 5 hours. The precipitate is filtered off on a suction filter.

Melting point: 275°–278° C.

Mass spectrum: M⁺=404

$R_f$: 0.81 (silica gel; methylene chloride/methanol/conc. ammonia=2:1:0.2)

(5) 5-[[4-(Isobutoxycarbonylmethoxy)phenyl]aminocarbonyl]-2-(4-piperidyl)-1,3,4-thiadiazole hydrochloride The reaction is carried out in isobutanol/ethereal hydrochloric acid (8:1). After evaporation of the ether, the mixture is heated at 80° C. for 5 hours. The residue is triturated with isobutanol and dried.

Melting point: 284°–286° C.

Mass spectrum: M$^+$=418

R$_f$: 0.83 (silica gel; methylene chloride/methanol/conc. ammonia=2:1:0.2)

(6) 5-[[4-(Ethoxycarbonylmethoxy)phenyl]aminocarbonyl]-2-(4-piperidyl)-1,3,4-thiadiazole hydrochloride The reaction is carried out in ethanol/ethereal hydrochloric acid (7:1). After evaporation of the ether, the mixture is heated under reflux for 6 hours. The residue is triturated with ethanol and dried.

Melting point: 265°–267° C.

Mass spectrum: M$^+$=390

R$_f$: 0.74 (silica gel; methylene chloride/methanol/conc. ammonia=4:1:0.2)

EXAMPLE 9

1-[1-(tert-Butoxycarbonyl)-4-piperidyl]-4-[[4-(methoxycarbonylmethoxy)phenyl]carbonylamino]imidazole Sufficient methylene chloride is added to a suspension of 340 mg of methyl α-(4-carboxyphenoxy)acetate in 10 ml of thionyl chloride such that a solution results. The mixture is stirred at room temperature for 2 hours and the solvent is evaporated. 430 mg of crude 4-amino-1-[1-(tert-butoxycarbonyl)-4-piperidyl]imidazole in 40 ml of ethyl acetate and 1.0 ml of triethylamine in 20 ml of tetrahydrofuran are added to this solid and the mixture is stirred at room temperature for 16 hours. The reaction solution is extracted with water, saturated sodium hydrogencarbonate solution and saturated sodium chloride solution. The organic phase is evaporated and the crude product is chromatographed on silica gel using methylene chloride/methanol/conc. ammonia (18:1:0.1).

Yield: 310 mg (42% of theory),

Mass spectrum: M$^+$=458

R$_f$: 0.52 (silica gel; methylene chloride/methanol/conc. ammonia=9:1:0.1)

EXAMPLE 10

2-[1-(Benzyloxycarbonyl)-4-piperidyl]-5-[[4-(ethoxycarbonylmethoxy)phenyl]oxymethyl]-1,3,4-thiadiazole A suspension of 3.0 g of 1-[[[4-(ethoxycarbonylmethoxy)phenyl]oxymethyl]carbonyl]-2-[(1-benzyloxycarbonyl-4-piperidyl)carbonyl]hydrazine and 2.4 g of 2,4-bis-(4-methoxyphenyl)-1,3-dithia-2,4-diphosphetane-2,4-disulphide in 500 ml of tetrahydrofuran is heated at reflux for 30 minutes. The solvent is evaporated under reduced pressure and the residue is chromatographed on silica gel using ethyl acetate/cyclohexane (2:1).

Yield: 2.1 g (70% of theory),

Melting point: 96°–98° C.

R$_f$: 0.45 (silica gel; methylene chloride/methanol/conc. ammonia=2:1:0.2)

The following compound is prepared analogously to Example 10:

(1) 2-[1-(Benzyloxycarbonyl)-4-piperidyl]-5-[2-[4-(ethoxycarbonylmethoxy)phenyl]ethyl]-1,3,4-thiadiazole Mass spectrum: M$^+$=509

R$_f$ value: 0.38 (silica gel; cyclohexane/ethyl acetate=1:2)

EXAMPLE 11

Dry ampoule containing 2.5 mg of active compound per 1 ml

Composition

| | |
|---|---|
| Active compound | 2.5 mg |
| Mannitol | 50.0 mg |
| Water for injection purposes to | 1.0 ml |

Preparation

Active compound and mannitol are dissolved in water. After filling the ampoule is freeze-dried. Dissolution to give the ready-to-use solution is carried out using water for injection purposes.

EXAMPLE 12

Dry ampoule containing 35 mg of active compound per 2 ml

Composition

| | |
|---|---|
| Active compound | 35.0 mg |
| Mannitol | 100.0 mg |
| Water for injection purposes to | 2.0 ml |

Preparation

Active compound and mannitol are dissolved in water. After filling the ampoule is freeze-dried. Dissolution to give the ready-to-use solution is carried out using water for injection purposes.

EXAMPLE 13

Tablet containing 50 mg of active compound

| | |
|---|---|
| (1) Active compound | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation (1), (2) and (3) are mixed and granulated with an aqueous solution of (4). (5) is added to the dry granules. From this mixture tablets are pressed which are biplanar with an edge on both sides and a breaking notch on one side. Diameter of the tablets: 9 mm.

EXAMPLE 14

Tablet containing 350 mg of active compound

Composition

| | |
|---|---|
| (1) Active compound | 350.0 mg |
| (2) Lactase | 136.0 mg |
| (3) Maize starch | 80.0 mg |
| (4) Polyvinylpyrrolidone | 30.0 mg |
| (5) Magnesium stearate | 4.0 mg |
| | 600.0 mg |

Preparation (1), (2) and (3) are mixed and granulated with an aqueous solution of (4). (5) is added to the dry granules. From this mixture, tablets are pressed which are biplanar with an edge on both sides and a breaking notch on one side. Diameter of the tablets: 12 mm.

EXAMPLE 15

Capsules containing 50 mg of active compound
Composition

| | | |
|---|---|---|
| (1) Active compound | 50.0 mg | |
| (2) Maize starch, dried | 58.0 mg | |
| (3) Lactose, powdered | 50.0 mg | |
| (4) Magnesium stearate | 2.0 mg | |
| | 160.0 mg | |

Preparation (1) is triturated with (3). This trituration is added to the mixture of (2) and (4) with intensive mixing.

This powder mixture is filled into hard gelatin capsules of size 3 on a capsule-filling machine.

EXAMPLE 16

Capsules containing 350 mg of active compound
Composition

| | | |
|---|---|---|
| (1) Active compound | 350.0 mg | |
| (2) Maize starch, dried | 46.0 mg | |
| (3) Lactose, powdered | 30.0 mg | |
| (4) Magnesium stearate | 4.0 mg | |
| | 430.0 mg | |

Preparation (1) is triturated with (3). This trituration is added to the mixture of (2) and (4) with intensive mixing.

This powder mixture is filled into hard gelatin capsules of size 0 on a capsule-filling machine.

What is claimed is:

1. A 1,3,4-thiadiazole of the formula

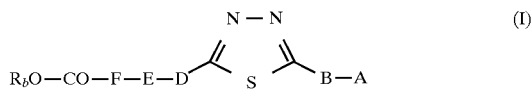

wherein

A is a cycloalkyl group having 5 to 7 carbon atoms, which is optionally substituted by 1 to 4 alkyl groups, in which an unsubstituted methylene group is replaced by the $R_a$—N< group, which may additionally be substituted by a cyano, aminocarbonyl, carboxyl, alkoxycarbonyl or phenylalkoxycarbonyl group or alternatively, if the substitution does not take place in the α-position relative to a nitrogen atom, by a hydroxyl, alkoxy or phenylalkoxy group, and in which $R_a$ is a hydrogen atom, an alkyl group, a phenylalkyl group, an alkoxycarbonyl group having a total of 2 to 6 carbon atoms, a phenylalkoxycarbonyl group, an alkenyloxycarbonyl group having a total of 4 to 6 carbon atoms, a cycloalkoxycarbonyl group having a total of 6 to 8 carbon atoms or an $R_1$—CO—O—($R_2$CH)—O—CO— group, in which $R_1$ is an alkyl group having 1 to 5 carbon atoms, a cycloalkyl group having 5 to 7 carbon atoms, a phenylalkyl group, an alkoxy group having 1 to 5 carbon atoms, a cycloalkoxy group having 5 to 7 carbon atoms or a phenyl group and $R_2$ is a hydrogen atom, an alkyl group having 1 to 4 carbon atoms, a cycloalkyl group having 5 to 7 carbon atoms or a phenyl group, and additionally in the 6- or 7-membered azacycloalkyl groups thus formed a >CH— unit in the 4-position may be replaced by a nitrogen atom or in the 5- to 7-membered azacycloalkyl groups thus formed a —CH$_2$—CH< unit may be replaced by a —CH=C< unit and in the piperazinyl or homopiperazinyl rings thus formed one or two methylene groups, which are adjacent to the nitrogen atom in the 4-position, may in each case be replaced by a carbonyl group, or a quinuclidinyl group, B is a bond or a straight-chain or branched alkylene group having 1 to 8 carbon atoms, an alkenylene group having 2 or 3 carbon atoms, an —O(CH$_2$)$_n$—, —(CH$_2$)$_n$O—, —S(CH$_2$)$_n$—, —(CH$_2$)$_n$S—, —CONR$_3$—, —R$_3$NCO—, —NR$_3$(CH$_2$)$_n$— or —(CH$_2$)$_n$NR$_3$— group, in which n is the number 1 or 2 and $R_3$ is a hydrogen atom, a phenylalkyl group which is optionally substituted in the phenyl nucleus by a fluorine, chlorine or bromine atom or by an alkyl, hydroxyl or alkoxy group, or is an alkyl or pyridylalkyl group, D is a —CO—NR$_3$—, —NR$_3$—CO—, —SO$_2$—NR$_3$—, —NR$_3$—SO$_2$—, —W—CO—NR$_3$—, —W$_1$—NR$_3$—CO—, —W$_1$—SO$_2$NR$_3$—, —W$_1$—NR$_3$SO$_2$—, —CO—NR$_3$—W$_1$—, —NR$_3$—CO—W$_1$—, —SO$_2$NR$_3$—W$_1$—, —NR$_3$SO$_2$—W$_1$—, —CO—(CH$_2$)$_n$—O—, —CO—(CH$_2$)$_n$—NR$_3$—, —O—W$_1$—, —W$_1$—O—, —S—W$_1$—, —W$_1$—, —W$_1$—S—, —NR$_3$—W$_1$—, —W$_1$—NR$_3$—, —(CH$_2$)$_n$—O—(CH$_2$)$_n$—, —(CH$_2$)$_n$—NR$_3$—(CH$_2$)$_n$—, —W— or —W—CO— group, in which $R_3$ and n are defined as mentioned above, $W_1$ is an alkylene group having 1 to 3 carbon atoms, $W_2$ is an alkenylene group having 2 or 3 carbon atoms and W is an alkylene group having 1 to 3 carbon atoms or an alkenylene group having 2 or 3 carbon atoms, E is a phenylene group which may be mono- or disubstituted by fluorine, chlorine or bromine atoms, or by alkyl, trifluoromethyl, $R_3$O— or $R_3$O—CO—CH$_2$—O— groups, it being possible for the substituents to be identical or different and $R_3$ being defined as mentioned above, a pyridinylene, pyrimidinylene, pyrazinylene, pyridazinylene or triazinylene group, each of which may be substituted in the carbon ring system by a chlorine atom or by an alkyl or alkoxy group, it additionally being possible for one or two —CH=N— groups each to be replaced by a —CO—NR$_3$— group, in which $R_3$ is defined as mentioned above, and one of the nitrogen atoms may also be bonded to the radical F, instead of to the radical $R_3$, if this is not a bond, a cycloalkylene group having 4 to 5 carbon atoms, which is optionally substituted by an alkyl, phenylalkyl or phenyl group, in which a >CH— unit may be replaced by a nitrogen atom and additionally a methylene group adjacent to the nitrogen atom may be replaced by a carbonyl group, or a cycloalkylene group, having 6 or 7 carbon atoms which is optionally substituted by an alkyl, phenylalkyl or phenyl group, in which one or two >CH— units may each be replaced by a nitrogen atom, it additionally being possible for a methylene group adjacent to a nitrogen atom to be replaced by a carbonyl group, F is a bond, a straight-chain or branched alkylene or alkenylene group, which is optionally substituted by a phenylalkyl, phenyl, pyridyl, $R_3O—$, $R_3S—$, $R_3R_3N—$, $R_3O—CO—$, $R_3R_3N—CO—$, $R_4CO—NR_3—$, $R_5O—CO—NR_3—$, $R_4SO_2—NR_3—$, $R_3R_3N—CO—NR_3—$, $R_3O—CO—C_{1-3}$-alkyl or $R_3R_3N—CO—C_{1-3}$-alkyl group, in which in each case the alkylene moiety may contain 1 to 5 carbon atoms and the alkenylene moiety may contain 2 to 5 carbon atoms, or a $—Y—W_1—$ group, in which $R_3$ and $W_1$ are defined as mentioned above, $R_4$ is an alkyl group having 1 to 5 carbon atoms, or a phenylalkyl, phenyl or pyridyl group, $R_5$ is an alkyl group having 1 to 5 carbon atoms, a phenylalkyl, cycloalkyl or cycloalkylalkyl group and Y is an oxygen atom, a $—CO—$, sulphenyl-, sulphinyl-, sulphonyl-, $—NR_3—$, $—N(COR_4)—$, $—N(SO_2R_4)—$, $—CO—NR_3—$ or $—NR_3—CO—$ group, Y being linked to the radical E, with the proviso that a heteroatom of the radical E is not bonded to a nitrogen or sulphur atom of the above groups, and $R_b$ is an alkyl group having 1 to 5 carbon atoms or a cycloalkyl group having 5 to 7 carbon atoms in the cycloalkyl moiety, it being possible for the above-mentioned groups each to be substituted in the alkyl and cycloalkyl moiety from position 2 by an $R_3O—$ or $R_3R_3N—$ group, or is an alkenyl group having 3 to 5 carbon atoms, a phenylalkyl group, a cycloalkyl-alkyl group having 3 to 7 carbon atoms in the cycloalkyl moiety, which may be substituted in the alkyl moiety from position 2 by an $R_3O—$ or $R_3R_3N—$ group, $R_3$ in each case being defined as mentioned above, an $R_1—CO—O—(R_2CH)—$ group, in which $R_1$ and $R_2$ are defined as mentioned above, or alternatively a hydrogen atom if the $R_bO—CO—$ group is not directly bonded to a nitrogen atom of the radical E, the distance between the furthest removed nitrogen atom of the group A and the $COOR_b$ group being at least 11 bonds, where, if nothing different has been mentioned, the above-mentioned alkyl, alkylene or alkoxy moieties may each contain 1 to 3 carbon atoms and the above-mentioned cycloalkyl moieties may each contain 3 to 7 carbon atoms, or a tautomer or physiologically tolerable salt thereof.

2. A 1,3,4-thiadiazole of the formula I according to claim 1, in which

A is a cycloalkyl group having 5 to 7 carbon atoms, which is optionally substituted by 1 to 4 alkyl groups, in which an unsubstituted methylene group is replaced by the $R_a—N<$ group, which may additionally be substituted by a cyano, aminocarbonyl, carboxyl or alkoxycarbonyl group or alternatively, if the substitution does not take place in the α-position relative to a nitrogen atom, by a hydroxyl or alkoxy group, and in which $R_a$ is a hydrogen atom, an alkyl, phenylalkyl, alkoxycarbonyl or phenylalkoxycarbonyl group or an $R_1—CO—O—(R_2CH)—O—CO—$ group, in which $R_1$ is an alkyl, cycloalkyl, phenyl, alkoxy or cycloalkoxy group each having 5 to 7 carbon atoms in the cycloalkyl moiety and $R_2$ is a hydrogen atom or a methyl group, and additionally in the 6- or 7-membered azacycloalkyl groups thus formed a $>CH—$ unit in the 4-position may be replaced by a nitrogen atom or in the 5- to 7-membered azacycloalkyl groups thus formed a $—CH_2—CH<$ unit may be replaced by a $—CH=C<$ unit, or a quinuclidinyl group, B is a bond or an alkylene group having 1 to 5 carbon atoms, an alkenylene group having 2 or 3 carbon atoms, or a $—OCH_2—$, $—CH_2O—$, $—SCH_2—$, $—CH_2S—$, $—CONR_3—$, $—R_3NCO—$, $—NR_3CH_2—$ or $—CH_2NR_3—$ group, in which $R_3$ is a hydrogen atom, or an alkyl, phenylalkyl or pyridylalkyl group, and an oxygen, sulphur or nitrogen atom of the radical B is not bonded directly to a nitrogen atom of the radical A or to a nitrogen atom of the 5-membered heterocycle, D is a $—CO—$, $—CO—NR_3—$, $—NR_3—CO—$, $—SO_2—NR_3—$, $—NR_3—SO_2—$, $—W—CO—NR_3—$, $—W_1—NR_3—CO—$, $—W_1—SO_2NR_3—$, $—W_1—NR_3SO_2—$, $—CO—NR_3—W_1—$, $—NR_3—CO—W_1—$, $—SO_2NR_3—W_1—$, $—NR_3SO_2—W_1—$, $—CO—CH_2—O—$, $—CO—CH_2—NR_3—$, $—O—W_1—$, $—W_1—O—$, $—S—W_1—$, $—W_1—S—$, $—NR_3—W_1—$, $—W_1—NR_3—$, $—CH_2—O—CH_2—$, $—CH_2—NR_3—CH_2—$, $—W_1—$ or $—W—CO—$ group, in which $R_3$ is defined as mentioned above, $W_1$ is an alkylene group having 1 to 3 carbon atoms, $W_2$ is an alkenylene group having 2 or 3 carbon atoms, and W is an alkylene group having 1 to 3 carbon atoms or an alkenylene group having 2 or 3 carbon atoms, E is a phenylene group which may be substituted by a fluorine, chlorine or bromine atom, or by an alkyl, trifluoromethyl, $R_3O—$ or $R_3O—CO—CH_2—O—$ group, $R_3$ being defined as mentioned above, a pyridinylene, pyrimidinylene, pyrazinylene or pyridazinylene group, each of which may be substituted in the carbon ring system by an alkyl or alkoxy group, a 1,4-cyclohexylene group, in which one or two $>CH—$ units may each be replaced by a nitrogen atom, it additionally being possible in each case for a methylene group adjacent to a nitrogen atom to be replaced by a carbonyl group, a 1,3-cyclohexylene group, in which a $>CH—$ unit may be replaced by a nitrogen atom, it then additionally being possible for a methylene group adjacent to the nitrogen atom to be replaced by a carbonyl group, a 1,3-pyrrolidinylene, 2-oxo-1,3-pyrrolidinylene, 5-oxo-1,3-pyrrolidinylene or 1,4-homopiperazinylene group, F is a bond, a straight-chain or branched alkylene group having 1 to 5 carbon atoms, which is optionally substituted by a phenyl, pyridyl, $R_3O—$, $R_4CO—NR_3—$, $R_5O—CO—NR_3—$, $R_4SO_2—NR_3—$, $R_3R_3N—CO—NR_3—$ or a $—Y—W_1—$ group, in which $R_3$ and $W_1$ are defined as mentioned above, $R_4$ is an alkyl group having 1 to 5 carbon atoms, or a phenylalkyl, phenyl or pyridyl group, $R_5$ is an alkyl group having 1 to 5 carbon atoms or a phenylalkyl group and Y is an oxygen atom, a sulphenyl, $—NR_3—$, $—N(COR_4)—$ or $—N(SO_2R_4)—$ group, Y being linked to the radical E, with the proviso that a heteroatom of the radical E is not bonded to a nitrogen or sulphur atom of the above groups, and $R_b$ is an alkyl group having 1 to 5 carbon atoms or a cycloalkyl group having 5 to 7 carbon atoms in the cycloalkyl moiety, each of which may be substituted in the alkyl and cycloalkyl moiety from position 2 by an $R_3O—$ or $R_3R_3N—$ group, or is an alkenyl group having 3 to 5 carbon atoms, a phenylalkyl group, a cycloalkylalkyl group having 3 to 7 carbon atoms in the cycloalkyl moiety, which may be substituted in the alkyl moiety from position 2 by an $R_3O—$ or $R_3R_3N—$ group, $R_3$ in each case being defined as mentioned above, an $R_1—CO—O—(R_2CH)—$ group, in which $R_1$ and $R_2$ are defined as mentioned above, or alternatively a hydrogen atom if the $R_bO—CO—$ group is not directly bonded to a nitrogen atom of the radical E, the distance between the furthest removed nitrogen atom of the group A and the $COOR_b$ group being at least 11 bonds, where, if nothing different has been mentioned, the above-mentioned alkyl, alkylene or alkoxy moieties may each contain 1 to 3 carbon atoms, or a tautomer or physiologically tolerable salt thereof.

3. A 1,3,4-thiadiazole of the formula I according to claim 1, in which

A is a cycloalkyl group having 5 or 6 carbon atoms, in which an unsubstituted methylene group in the 3- or 4-position is replaced by the $R_a—N<$ group, in which $R_a$ is a hydrogen atom, or a $C_{1-2}$-alkyl, $C_{1-4}$-alkoxycarbonyl or benzyloxycarbonyl group, and additionally in the 4-piperidinyl groups thus formed a $>CH—$ unit in the 4-position may be replaced by a nitrogen atom, B is a bond, a $C_{1-2}$-alkylene, $—OCH_2—$ or $—CH_2O—$ group, D is a $—CO—$, $—CO—NR_3—$, $—NR_3—CO—$, $—W—CO—NR_3—$, $—CO—NR_3—W_1—$, $—NR_3—CO—W_1$, $—CO—CH_2—O—$, $—O—W_1—$, $—W_1—O—$, $—W_1—$ or $—W—CO—$ group, in which $R_3$ is a hydrogen atom, or a $C_{1-4}$-alkyl, benzyl or pyridylmethyl group, $W_1$ is a $C_{1-2}$-alkylene group and W is a $C_{1-2}$-alkylene or vinylene group, E is a 1,4-phenylene group which may be substituted by a hydroxyl, methoxy, carboxymethoxy or methoxycarbonylmethoxy group, a 1,4-cyclohexylene group in which one or two $>CH—$ units may each be replaced by a nitrogen atom, F is a bond, a straight-chain or branched alkylene group having 1 to 3 carbon atoms, which is optionally substituted by an $R_4CO—NR_3—$, $R_4SO_2—NR_3—$ or $—Y—W_1—$ group, in which $R_3$ and $W_1$ are defined as mentioned above, $R_4$ is a methyl, ethyl or phenyl group and Y is an oxygen atom, or an $—NR_3—$ or $—N(SO_2R_4)—$ group, Y being linked to the radical E, with the proviso that a nitrogen atom of the radical E is not bonded to a nitrogen atom of the above groups, and $R_3$ and $R_4$ are defined as mentioned above, and $R_b$ is a $C_{1-5}$-alkyl, cyclohexyl or benzyl group or alternatively a hydrogen atom if the $R_bO—CO—$ group is not directly bonded to a nitrogen atom of the radical E, the distance between the furthest removed nitrogen atom of the group A and the $COOR_b$ group being at least 11 bonds, or a tautomer or physiologically tolerable salt thereof.

4. A 1,3,4-thiadiazole of the formula I according to claim 1, in which

A is a cyclohexyl group, in which an unsubstituted methylene group in the 4-position is replaced by the $R_a—N<$ group, in which $R_a$ is a hydrogen atom, a $C_{1-4}$-alkoxycarbonyl or benzyloxycarbonyl group, B is a bond or a $C_{1-2}$-alkylene group, D is a $—CH_2CH_2—$, $—CO—$, $—CH_2—O—$, $—CH_2CH_2—CO—$, $—CH=CH—CO—$, $—CO—NR_3—$, $NR_3—CO—$, $—CH_2CH_2—CO—NR_3—$, $—CO—NR_3—CH_2—$ or $—CO—NR_3—CH_2CH_2—$ group, in which $R_3$ is a hydrogen atom or a pyridylmethyl group, E is a 1,4-phenylene, 1,4-cyclohexylene, 1,4-piperidinylene or 1,4-piperazinylene group, F is a bond, a $—CH_2—$, $—CH_2CH_2—$, $—O—CH_2—$, $—O—CH_2CH_2—$ or $—N(SO_2CH_3)—CH_2—$ group, and $R_b$ is a $C_{1-4}$-alkyl or cyclohexyl group or alternatively a hydrogen atom if the $R_bO—CO—$ group is not directly bonded to a nitrogen atom of the radical E, the distance between the furthest removed nitrogen atom of the group A and the $COOR_b$ group being at least 11 bonds, or a tautomer or physiologically tolerable salt thereof.

5. A compound selected from the group consisting of:

(a) 5-[[trans-4-(2-carboxyethyl)cyclohexyl]aminocarbonyl]-2-(4-piperidyl)-1,3,4-thiadiazole, and (b) 5-[[4-(carboxymethoxy)phenyl]aminocarbonyl]-2-(4-piperidyl)-1,3,4-thiadiazole, or a $C_{1-4}$-alkyl or cyclohexyl ester thereof, or a physiologically tolerable salt thereof.

6. 5-[[trans-4-(2-carboxyethyl)cyclohexyl]aminocarbonyl]-2-(4-piperidyl)-1,3,4-thiadiazole or a physiologically tolerable salt thereof.

7. A pharmaceutical composition comprising a compound in accordance with claim 1, 2, 3, 4, 5 or 6 and a pharmaceutically acceptable carrier.

8. A method for the treatment or prevention of venous or arterial thromboses which comprises administering to a host suffering from or likely to suffer from the formation of a thrombus an anti-thrombotic amount of a compound in accordance with claim 1, 2, 3, 4, 5 or 6.

* * * * *